United States Patent
Gibson et al.

(10) Patent No.: US 6,413,536 B1
(45) Date of Patent: Jul. 2, 2002

(54) HIGH VISCOSITY LIQUID CONTROLLED DELIVERY SYSTEM AND MEDICAL OR SURGICAL DEVICE

(75) Inventors: John W. Gibson, Springville; Stacey A. Sullivan, Birmingham; John C. Middleton, Birmingham; Arthur J. Tipton, Birmingham, all of AL (US)

(73) Assignee: Southern Biosystems, Inc., Birmingham, AL (US)

( * ) Notice: Subject to any disclaimer, the term of this patent is extended or adjusted under 35 U.S.C. 154(b) by 0 days.

(21) Appl. No.: 09/385,107

(22) Filed: Aug. 27, 1999

Related U.S. Application Data

(63) Continuation-in-part of application No. 08/944,022, filed on Sep. 15, 1997, now Pat. No. 5,968,542, which is a continuation-in-part of application No. 08/478,450, filed on Jun. 7, 1995, now abandoned, and a continuation-in-part of application No. 08/474,337, filed on Jun. 7, 1995, now Pat. No. 5,747,058.

(51) Int. Cl.[7] .............................. A61F 2/02; A61F 13/02; A61K 9/14; B32B 5/16; B01J 13/02
(52) U.S. Cl. .................. 424/423; 424/435; 424/443; 424/484; 428/402.21; 264/4.1
(58) Field of Search .................................. 424/423, 443, 424/484, 435; 428/402.21; 264/4.1

(56) References Cited

U.S. PATENT DOCUMENTS

| | | |
|---|---|---|
| 2,931,802 A | 4/1960 | Toney |
| 3,853,837 A | 12/1974 | Fujino et al. |
| 3,992,365 A | 11/1976 | Beddell et al. |
| 4,024,248 A | 5/1977 | Konig et al. |
| 4,100,274 A | 7/1978 | Dutta et al. |
| 4,411,890 A | 10/1983 | Momany |

(List continued on next page.)

FOREIGN PATENT DOCUMENTS

| | | |
|---|---|---|
| DE | 1569231 | 9/1964 |
| DE | 1 569 231 | 8/1969 |
| DE | 2213717 | 11/1972 |
| DE | 2321174 | 11/1973 |
| DE | 2438352 | 2/1976 |
| DE | 2720245 | 11/1977 |
| DE | 19714765 A | * 10/1998 |
| EP | 0290983 A | * 11/1988 |
| EP | 0 539 559 A1 | 10/1992 |
| EP | 0 537 559 A1 | 4/1993 |

(List continued on next page.)

OTHER PUBLICATIONS

"3M DDS Announces Development of New HFA–Compatible Excipients: Novel Oligomeric Acids as MDI Suspension Aids and Solubilizers," 3M Delivery Newsletter, 3M Drug Delivery Systems, vol. 15, Jun. 2000.

Ajayaghosh, A., et al., "Solid–Phase Synthesis of N–Methyl and N–Ethylamides of Peptides Using Photolytically Detachable ((3–Nitro–4–((alkylamino)methyl) benzamido)methyl)polystrene Resin," J. Org. Chem., 55:2826 (1990).

(List continued on next page.)

Primary Examiner—Carlos Azpuru
(74) Attorney, Agent, or Firm—Bruce D. Gray, Esq.; Kilpatrick Stockton LLP

(57) ABSTRACT

The present invention relates to novel nonpolymeric compounds and compositions that form liquid, high viscosity materials suitable for the delivery of biologically active substances in a controlled fashion, and for use as medical or surgical devices. The materials can optionally be diluted with a solvent to form a material of lower viscosity, rendering the material easy to administer. This solvent may be water insoluble or water soluble, where the water soluble solvent rapidly diffuses or migrates away from the material in vivo, leaving a higher viscosity liquid material.

58 Claims, 4 Drawing Sheets

U.S. PATENT DOCUMENTS

| | | |
|---|---|---|
| 4,530,840 A | 7/1985 | Tice et al. |
| 4,622,219 A | 11/1986 | Haynes |
| 4,725,442 A | 2/1988 | Haynes |
| 4,767,628 A | 8/1988 | Hutchinson |
| 4,891,225 A | 1/1990 | Langer |
| 4,906,474 A | 3/1990 | Langer |
| 4,938,763 A | 7/1990 | Dunn et al. |
| 4,957,744 A | 9/1990 | Della Valle et al. |
| 5,149,543 A | 9/1992 | Cohen |
| 5,278,201 A | 1/1994 | Dunn et al. |
| 5,278,202 A | 1/1994 | Dunn et al. |
| 5,324,519 A | 6/1994 | Dunn et al. |
| 5,324,520 A | 6/1994 | Dunn et al. |
| 5,330,835 A | 7/1994 | Kikuchi et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,391,381 A | 2/1995 | Wong et al. |
| 5,399,363 A | 3/1995 | Liversidge et al. |
| 5,487,898 A | 1/1996 | Lu et al. |
| 5,545,408 A | 8/1996 | Trigg et al. |
| 5,569,450 A | 10/1996 | Duan et al. |
| 5,599,552 A | 2/1997 | Dunn et al. |
| 5,702,716 A | 12/1997 | Dunn et al. |
| 5,725,841 A | 3/1998 | Duan et al. |
| 5,733,950 A | 3/1998 | Dunn et al. |
| 5,736,152 A | 4/1998 | Dunn |
| 5,739,176 A | 4/1998 | Dunn et al. |
| 5,747,058 A | 5/1998 | Tipton et al. |
| 5,750,100 A | 5/1998 | Yamagata et al. |
| 5,759,563 A | 6/1998 | Yewey et al. |
| 5,780,044 A | 7/1998 | Yewey et al. |
| 5,840,329 A | 11/1998 | Bai |
| 5,968,542 A | 10/1999 | Tipton |
| 6,042,811 A | 3/2000 | Duan et al. |
| 6,051,558 A | 4/2000 | Burns et al. |
| 6,126,919 A | 10/2000 | Stefely et al. |

FOREIGN PATENT DOCUMENTS

| | | | |
|---|---|---|---|
| EP | 0 539 751 A1 | | 5/1993 |
| EP | 0635531 A | * | 1/1995 |
| EP | 0711548 A | * | 5/1996 |
| EP | 0 773 034 A1 | | 5/1997 |
| EP | 0 537 559 B1 | | 1/1998 |
| EP | 0 539 751 B1 | | 2/1998 |
| JP | 2-96516 | | 4/1990 |
| JP | 2096516 | | 4/1990 |
| JP | 7115901 | | 5/1995 |
| JP | 7-115901 | | 5/1998 |
| WO | WO 91/18016 A1 | | 11/1991 |
| WO | WO 93/07833 A2 | | 4/1993 |
| WO | WO9415587 A | * | 7/1994 |
| WO | WO 95/17901 | | 7/1995 |
| WO | WO 95/17901 A1 | | 7/1995 |
| WO | WO 96/39995 A1 | | 12/1996 |
| WO | WO 96/39995 | | 12/1996 |
| WO | WO 97/15285 | | 5/1997 |
| WO | WO 97/15285 A1 | | 5/1997 |
| WO | WO 98/7962 A2 | | 7/1998 |
| WO | WO 98/27962 | | 7/1998 |
| WO | WO 98/27963 | | 7/1998 |
| WO | WO 98/27963 A2 | | 7/1998 |
| WO | WO 98/34596 A2 | | 8/1998 |
| WO | WO 98/34596 | | 8/1998 |
| WO | WO 98/34596 A3 | | 11/1998 |
| WO | WO 98/53837 A1 | | 12/1998 |
| WO | WO9913913 A | * | 3/1999 |
| WO | WO 00/78335 A1 | | 12/2000 |
| WO | WO0087335 A | * | 12/2000 |

OTHER PUBLICATIONS

Barb, R. et al., "Evaluation of the Saber Delivery System for the Controlled Release of Deslorelin: Effect of Dose in Estrogen Primed Ovarectomized Gilts," Proceed. Int'l Symp. Control. Rel. Bioact. Mater., 26 (1999).

Becker, S.E., et al. "Effects of Gonadotropin–Releasing Hormone Infused in a Pulsatile or Continuous Fashion on Serum Gonadotropin Concentrations and Ovulation in the Mare," *J. Anim. Sci.* (1992) 70:1208–1215.

Betschart, R., et al., "Evaluation of the Saber™ Delivery System for the Controlled Release of the GnRH Analogue Deslorelin for Advancing Ovulation in Mares: Effect of Gamma Radiation," Proceed. Int'l Symp. Control. Rel. Bioact. Mater. 25 (1998) Controlled Release Society, Inc. pp. 655–656.

Bühler, K., GnRH Agonists and Safety, In *GnRH Analagoues The State of the Art 1993*, A Summary of the 3rd International Symposium on GnRH Analogues in Cancer and Human Reproduction, Geneva, Feb. 1993.

Burns, P. et al., "Pharmacodynamic Evaluation of the Saber™ Delivery System for the Controlled Release of the GnRH Analogue Deslorelin Acetate for Advancing Ovulation in Cyclic Mares," Proceed. Int'l. Symp. Control. Rel. Bioact. Mater., 24 (1997), Controlled Release Society, Inc.

Coy, et al., "Solid Phase Synthesis of Luteinizing Hormone–Releasing Hormone and Its Analogs," *Methods Enzymol.* 37, 416 (1975).

Desai, Neil P., et al. "Surface Modifications of Polymeric Biomaterials for Reduced Thrombogenicity," *Polymeric Materials Science and Engineering*, vol. 62, 1990 by ACS.

Duan, D. et al., "Novel Dispersing Aids for Hydrofluoroalkane–Based Metered Dose Inhalers," 1998 Conference of the American Association of Pharmaceutical Scientists, San Francisco, California, Nov. 1998.

Duan, D. et al., "Oligomeric Lactic Acids as Solubilizing Aids for HFA–Based Metered Dose Inhalers," 1998 Conference of the American Association of Pharmaceutical Scientists, San Francisco, California, Nov. 1998.

Fitzgerald, B.P, et al., "Effect of Constant Administration of a Gonadotropin–Releasing Hormone Agonist on Reproductive Activity in Mares: Preliminary Evidence on Suppression of Ovulation During the Breeding Season," *Am. J. Vet. Res.*, 54:10 1746–.

Fleury, J., et al., "Evaluation of the Saber™ Delivery System for the Controlled Release of the Deslorelin for Advancing Ovulation in the Mare: Effects of Formulation & Dose," *Proceed. Int'l. Symp. Control. Rel. Bioact. Mater.* 25 (1998) Controlled Release Society, Inc. pp. 657–658.

Ginter, O.J., Reproductive Biology of the Mare: Basic and Applied Aspects, *EquiServices*, Chapter 12, 499–508 Cross Plains, Wisconsin (1970).

Ginther, O.J. et al. "Effect of a Synthetic Gonadotropin–Releasing Hormone on Plasma Concentrations of Luteinizing Hormone in Ponies," *Am. J. Vet. Res.*, 35: 79–81 (1974).

Ginther, O.J., "Ultrasonic Imaging and Reproductive Events in the Mare," *Equiservices*, Cross Plains, WI Chapter 4:43–72 (1986).

Harrison, L., et al. "Comparison of HCG, Buserelin and Luprostiol for Induction of Ovulation in Cyclling Mares," *J. Eq. Vet. Sci.*, 11:163–166 (1991).

Henry, C. "Surcrose Acetate Isobutyrate Special Grade for Beverage Applications".

Hyland, J.H., et al. "Infusion of Gonadotrophin–Releasing Hormone (GnRH) Induces of Ovulation and Fertile Oestrus in Mares During Seasonal Anoestrus," *J. Reprod. Fert.*, Suppl. 35 (1987), 211–220.

Irvine, C.H.G., "GnRH Clinical Application," In *Equine Reproduction*, (eds) McKinon, A.O. and Voss, J.L., Chapter 36, pp. 41–45, Lea & Febiger (1993).

Irvine, D.S., "Duration of Oestrus and Time of Ovulation in Mares Treated with Synthetic GnRH (Ay24,031)," *J. Reprod. Fert. Supp.* 23:279–283 (1975).

Jochle, W., et al., Control of Ovulation in the Mare with Ovuplant™, a Short–Term Release Implant (STI) Containing the GNRH Analogue Deslorelin Acetate: *J. Eq. Vet. Sci.*, 44:632 (1994).

Kulkarni et al., "Polyactic Acid for Surgical Implants," Arch. Surg., 93:389 (1966).

LaCoste, D., et al., "Reversible Inhibition of Testicular Androgen Secretion by 3–, 5–and 6–Month Controlled –Release Microsphere Formulations of teh LH–RH Agonist [D–Trp$^6$, des–Gly–NH$_2{}^{10}$] LH–RH Ethylamide in the Dog," *J. Steroid Biochem.* 33:5, 1007–1011 (1989).

Loy, R.G. et al. "The Effects of Human Chorionic Gonadotrophin on Ovulation, Length of Estrus, and Fertility in the Mare," *Cornell Vet.* 56:41–50 (1966).

Material Safety Data Sheet of Eastman Chemical Products, "SAIB" Sucrose Acetate Isobutyrate, pp. 2–18.

Material Safety Data Sheet of Eastman Fine Chemical Pharmaceutical Ingredients, Sucrose Acetate Isobutyrate Special Grade (SAIB–SG), Publication No. EFC–211, (May 1991).

Material Safety Data Sheet of Eastman Products for the Food Industry, "Sucrose Acetate Isbutyrate (SAIB–SB) for Use in Fruit–Flavored Beverages," Publication No. ZM–90, pp. 2–7 (Sep. 1989).

Mearns, "Changing Seasons," *The Blood–Horse*, Sep. 28, 1996, p. 4794–4795.

McCarthy, P. et al., "Management of Stallions on Large Breeding Farms," *Stallion Management*, vol. 8, No. 1, Apr. 1992, pp. 219–235.

McKinnon, A.O., et al. "Effect of a GnRH Analogue (Ovuplant), hCG and Dexamethasone on Time to Ovulation in Cycling Mares." *World Equine Veterinary Review*, (1997) 2:3 16–18.

McKinnon, A.O., et al. "Repeated Use of a GnRH Analogue Deslorelin (Ovuplant) for Hastening Ovulation in the Transitional Mare," *Equine Vet. J.*, (1996) 29:2 153–155.

Merrifield, B., *Science* 232:342 (1986).

Montovan, S.M., et al., "The Effect of a Potent GnRH Agonist on Gonadal and Sexual Activity in the Horse," *Theriogenology*, 33:6, 1305–1321 (1990).

Mumford, E.L. et al., "Use of Deslorelin Short–Term Implants to Induce Ovulation in Cycling Mares During Three Consecutive Estrov Cycles," *Animal Reproduction Science*, 139 (1995) 129–140.

Nett et al., "Further Studies on the Radioimmunoassay of Gonadotropin–Releasing Hormone: Effect of Radioiodination, Antiserum and Unextracted Serum on Levels of Immunoreactivity in Serum," *Endocrinology* 101:1135 (1977).

Rabb et al., "Effects of Active Immunication Against GnRH on LH, FSH and Prolactin Storage, Sectretion and Response to Their Secretagogues in Pony Geldings," *J. Anim. Sci.*, 68:3322–3329 (1990).

Roser, J.J., et al., "The Development of Antibodies to Human Chorionic Gonadotrpins Following its Repeated Injection in the Cyclic Mare," *J. Reprod. Fert. Suppl.*, 173–179 (1979).

Sullivan, J., "Duration of Estrus and Ovulation Time in Nonlactating Mares Given Human Chorionic Gonadotropin During Three Successive Estrous Periods," *J. Am. Vet. Med. Assoc.*, 63:895 (1973).

Thompson, Jr., D.L., et al., "Effects of Melatonin and Thyrotropin Releasing Hormone of Mares Durign the Nonbreeding Season," *J. Anim. Sci.*, 58:3, 668–677(1983).

Thompson, Jr., D.L., et al., "Testosterone Effects on Mares During Synchoronization with Altrenogest: FSH, LH, Estrous, Duration and Pregnancy Rate," *J. Anim. Sci.*, 56:3, 678–686 (1983).

Voss, J.L. et al. "The Effect of HCG on Duration of Oestrus, Ovulation Time and Fertility in Mares," *J. Reprod. Fert.*, Suppl. 23 (1975) 297–301.

Ansel, H.C. et al., *Pharmaceutical Dosage Forms and Drug Delivery System*, sixth ed., (1995).

Desai et al., "Surface Modification of Polymeric Biomaterials for Reduced Thrombogenicity," *Polym. Mater. Sci. Eng.*, 62:731–735 (1991).

Material Safety Data Sheet of Eastman Fine Chemicals, "Sucrose Acetate Isobutyrate, Special Grade (SAIB–SG)," Publication No. EFC–211, May 1991.

* cited by examiner

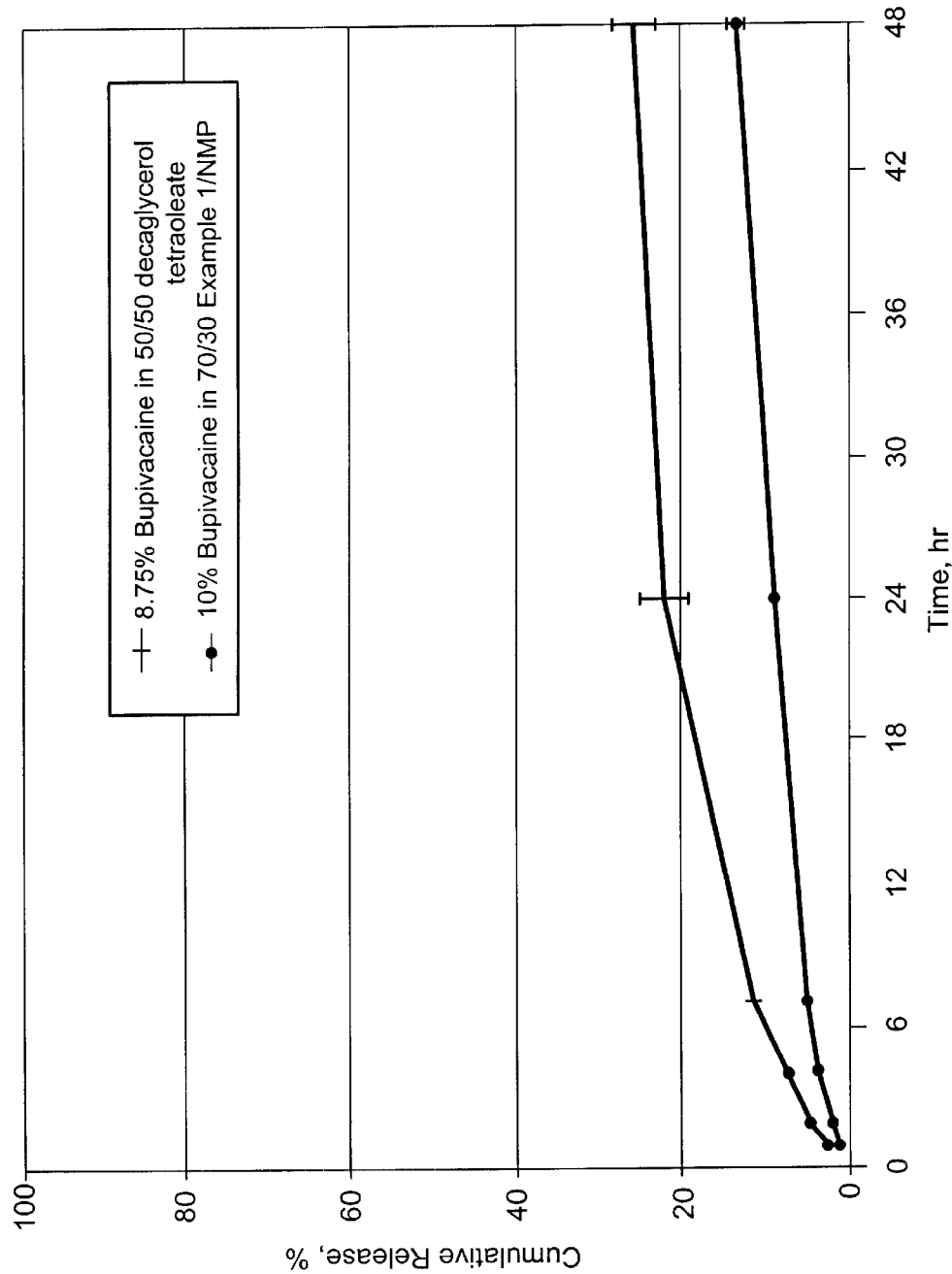
Figure 1. In Vitro Release of Bupivacaine from Biodegradable Ester/Solvent Mixtures

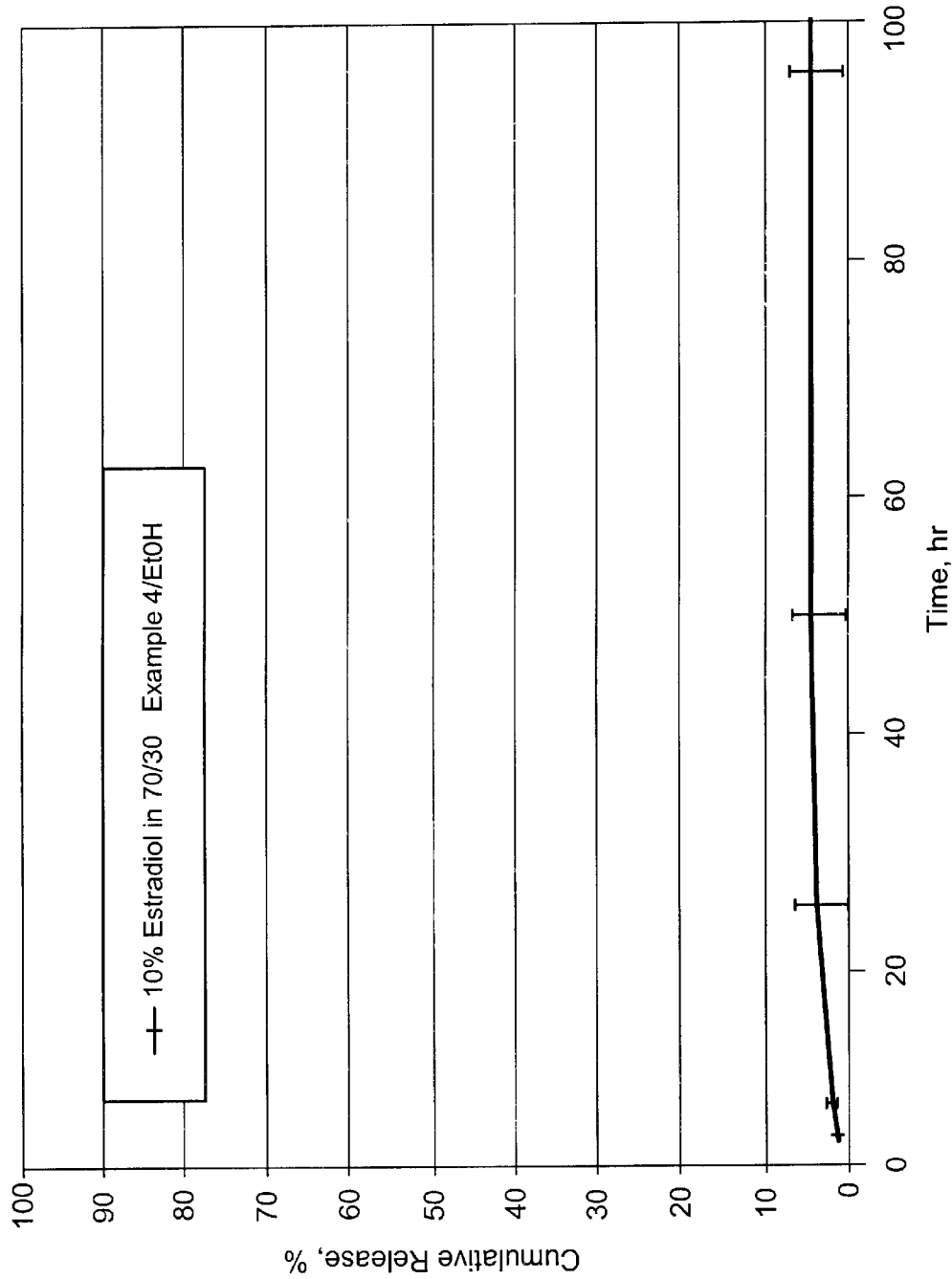

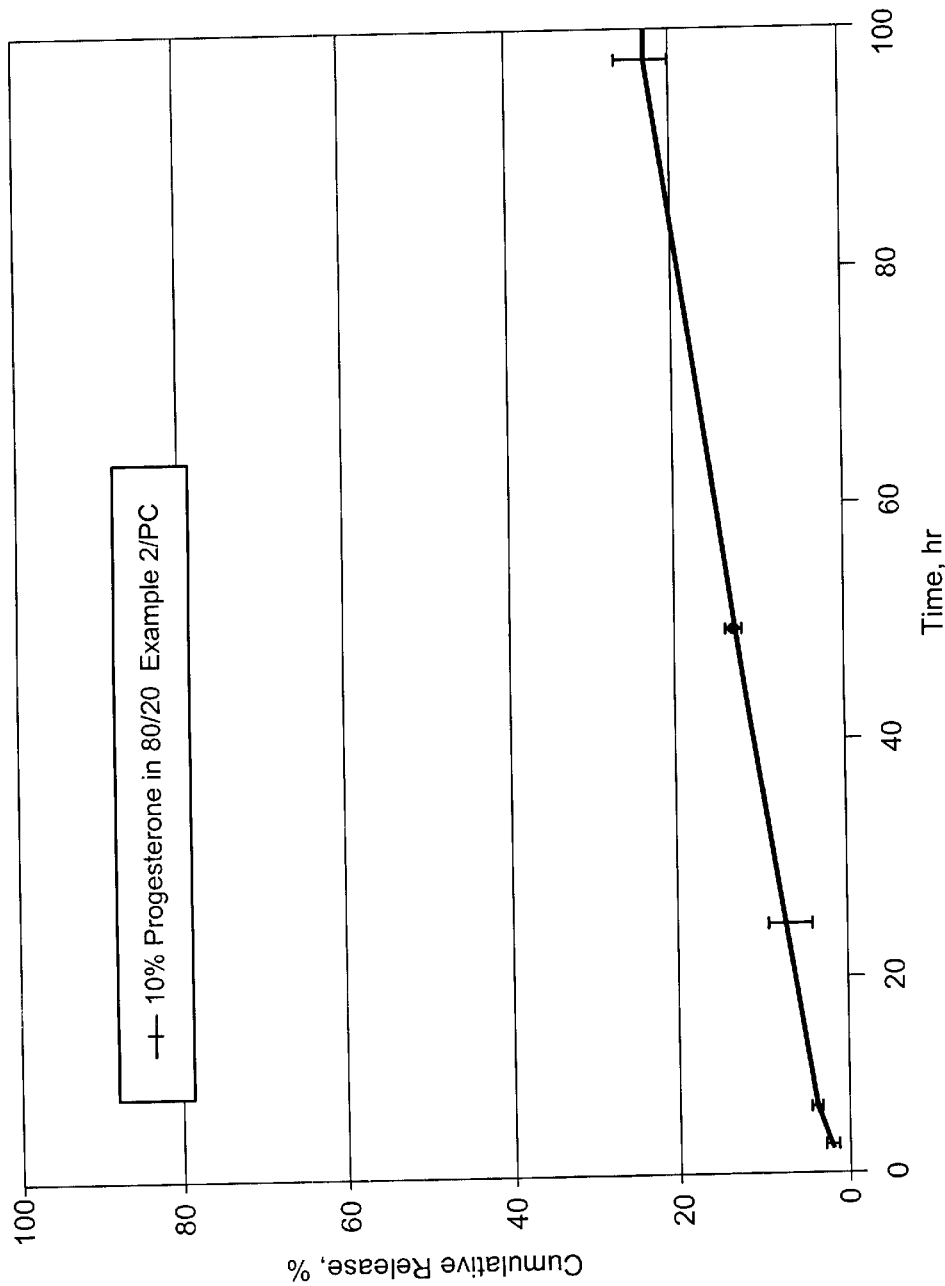
Figure 3. In Vitro Release of Progesterone from Biodegradable Ester/Solvent Formulation

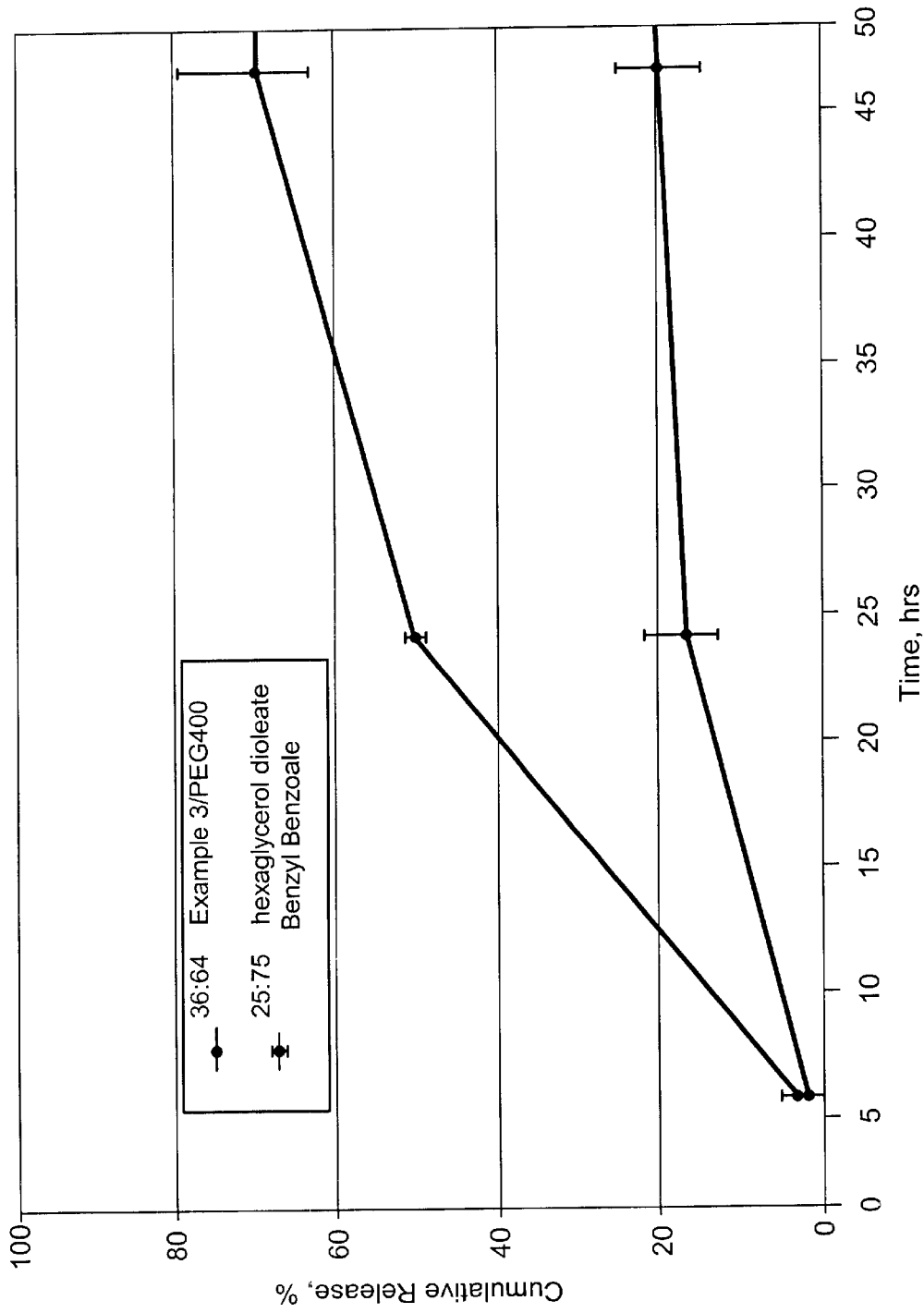

HIGH VISCOSITY LIQUID CONTROLLED DELIVERY SYSTEM AND MEDICAL OR SURGICAL DEVICE

This application is a continuation-in-part of U.S. Ser. No. 08/944,022, filed Sep. 15, 1997, now U.S. Pat. No. 5,968,542, which is a continuation-in-part of U.S. Ser. No. 08/478,450, filed Jun. 7, 1995, now abandoned, and which is a continuation-in-part of U.S. Ser. No. 08/474,337, filed Jun. 7, 1995, now U.S. Pat. No. 5,747,058, the entire contents of each of which are hereby incorporated by reference.

BACKGROUND OF THE INVENTION

1. Field of the Invention

The present invention relates to novel nonpolymeric compounds and compositions that form liquid, high viscosity materials suitable for the delivery of biologically active substances in a controlled fashion, and for use as medical or surgical devices. The materials can optionally be diluted with a solvent to form a material of lower viscosity, rendering the material easy to administer. This solvent may be water insoluble or water soluble, where the water soluble solvent rapidly diffuses or migrates away from the material in vivo, leaving a higher viscosity liquid material.

2. Description of Related Art

There has been extensive research in the area of biodegradable controlled release systems for bioactive compounds. Biodegradable matrices for drug delivery are useful because they obviate the need to remove the drug-depleted device.

The most common matrix materials for drug delivery are polymers. The field of biodegradable polymers has developed rapidly since the synthesis and biodegradability of polylactic acid was reported by Kulkarni et al., in 1966 ("Polylactic acid for surgical implants," *Arch. Surg.*, 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyethylenes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), U.S. Pat. No. 4,530,840 to Tice, et al. (polylactide, polyglycolide, and copolymers), and U.S. Pat. No. 5,234,520 (Dunn et al., biodegradable polymers for controlled delivery in treating periodontal disease).

Degradable materials of biological origin are well known including, for example, crosslinked gelatin. Hyaluronic acid has been crosslinked and used as a degradable swelling polymer for biomedical applications (U.S. Pat. No. 4,957,744 to Della Valle et al.; (1991) "Surface modification of polymeric biomaterials for reduced thrombogenicity," *Polym. Mater. Sci. Eng.*, 62:731–735]).

Biodegradable hydrogels have also been developed for use in controlled drug delivery as carriers of biologically active materials such as hormones, enzymes, antibiotics, antineoplastic agents, and cell suspensions. Temporary preservation of functional properties of a carried species, as well as the controlled release of the species into local tissues or systemic circulation, have been achieved. See for example, U.S. Pat. No. 5,149,543 to Cohen. Proper choice of hydrogel macromers can produce membranes with a range of permeability, pore sizes and degradation rates suitable for a variety of applications in surgery, medical diagnosis and treatment.

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few nanometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a non-reactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

While a number of materials have been evaluated for use in the controlled delivery of substances, there remains a need to provide more simple systems with low toxicity for the controlled delivery of substances. The delivery systems described above, for example, require the preparation of polymers and loaded polymeric matrices, or hydrogels, or other complex or fragile compositions. In particular, there is a need to provide a liquid-based delivery system that is easily formulated with a substance to be delivered and easily administered.

Therefore, it is an object of the invention to provide a simple system for the delivery of substances.

It is another object of the invention to provide a liquid-based delivery system that is easily formulated with a substance to be delivered and easily administered.

It is another object of the present invention to provide a method for the controlled delivery of substances in a simple liquid-based system.

SUMMARY OF THE INVENTION

The invention relates to compounds, and to compositions containing them, as well as to methods of using these compounds and compositions as delivery vehicles, for example as controlled delivery vehicles, for substances, such as bioactive substances. The invention also relates to these compounds, compositions, and methods of using them as medical or surgical devices, such as medical or surgical implants, films, or graft compositions. The compositions are generally in liquid form, and contain at least one non-water soluble, high viscosity, liquid carrier material comprising a nonpolymeric ester or mixed ester of one or more carboxylic acids, having a viscosity of at least 5,000 cP at 37° C., that does not crystallize neat under ambient or physiological conditions. The compositions can be dissolved in a physiologically acceptable solvent to lower their viscosity, rendering them easier to administer. After administration of compositions containing water-soluble solvents, however, the solvent diffuses or otherwise dissipates away from the material, which thus increases significantly in viscosity, and thereby forms a controlled release matrix for a bioactive substance, or a medical or surgical implant, film, or graft. Non-water soluble solvents may also be used, but will diffuse away from the nonpolymeric ester or mixed ester much more slowly.

Dissolution in solvent is particularly useful with nonpolymeric esters or mixed esters having very high viscosities, e.g., on the order of 100,000 cP at 37° C. Some nonpolymeric esters or mixed esters suitable for use in the invention, while having viscosities above 5,000 cP at 37° C., are not as viscous, and may be administered neat, i.e., without the addition of a solvent.

In another aspect, the invention relates to a method of administering a biologically active substance to a plant or an animal (including humans) by administering to the plant or animal a composition containing a non-water soluble, high viscosity, liquid carrier material comprising a nonpolymeric ester or mixed ester of one or more carboxylic acids, having a viscosity of at least 5,000 cP at 37° C., that does not crystallize neat under ambient or physiological conditions and a biologically active substance. The particular method of administration may vary, and may include topical, oral (e.g., as a solution, emulsion, or in a gelatin capsule), nasal, pulmonary, rectal, vaginal, or injectable routes for animals, and topical or injectable routes for plants.

In another aspect, the invention relates to a medical or surgical implant, film, or graft composition containing a non-water soluble, high viscosity, liquid carrier material comprising a nonpolymeric ester or mixed ester of one or more carboxylic acids, having a viscosity of at least 5,000 cP at 37° C., that does not crystallize neat under ambient or physiological conditions.

In yet another aspect, the invention relates to a method for the in vivo formation of an implant, film, or graft in a patient in need thereof, including:

(1) contacting a mixture containing:
  (a) a non-water soluble, high viscosity, liquid carrier material comprising a nonpolymeric ester or mixed ester of one or more carboxylic acids, having a viscosity of at least 5,000 cP at 37° C., that does not crystallize neat under ambient or physiological conditions; and
  (b) a solvent in which the non-polymeric, non-water soluble liquid carrier material is soluble; wherein the mixture has a viscosity of less than approximately 6000 cP at 37° C.; with the tissue of the patient; and (2) allowing the solvent to dissipate or diffuse into the tissue of the patient, thereby forming an implant, film, or graft of the non-polymeric, non-water soluble, high viscosity liquid carrier material. In an even more particular aspect of the invention, the mixture has as viscosity of less than approximately 4,000 cP, even more particularly, less than approximately 1,000 cP, at 37° C.

In yet another aspect, the invention relates to novel compounds having a structure selected from the group consisting of:

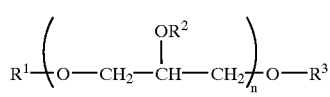

II wherein $R^1$, $R^2$, and $R^3$ are independently selected from the group consisting of hydrogen, alkanoyl having 2 to 6 carbons, hydroxy-substituted alkanoyl having 2 to 6 carbons, and acyloxy-substituted alkanoyl having 2 to 6 carbons, wherein n is between 1 and 20, and wherein at least one of $R^1$, $R^2$, and $R^3$ is other than hydrogen;

III wherein n is an integer between 4 and 8, and $R^1$ and $R^2$ are independently selected from the group consisting of hydrogen, alkanoyl having 2 to 6 carbons, hydroxy-substituted alkanoyl having 2 to 6 carbons, and acyloxy-substituted alkanoyl having 2 to 6 carbons, and wherein at least one of $R^1$ and $R^2$ is other than hydrogen;

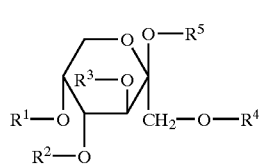

IV

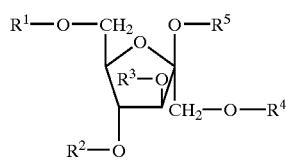

V wherein $R^1$, $R^2$, $R^3$, $R^4$, and $R^5$ are independently selected from the group consisting of hydrogen, alkanoyl having 2 to 6 carbons, hydroxy-substituted alkanoyl having 2 to 6 carbons, and acyloxy-substituted alkanoyl having 2 to 6 carbons, and wherein at least one of $R^1$, $R^2$, $R^3$, $R^4$, and $R^5$ is other than hydrogen;

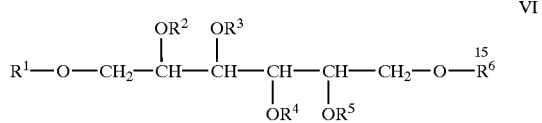

VI

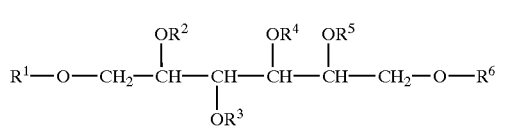

VII wherein $R^1$, $R^2$, $R^3$, $R^4$, $R^5$, and $R^6$ are independently selected from the group consisting of hydrogen, alkanoyl having 2 to 6 carbons, hydroxy-substituted alkanoyl having 2 to 6 carbons, and acyloxy-substituted alkanoyl having 2 to 6 carbons, and wherein at least one of $R^1$, $R^2$, $R^3$, $R^4$, $R^5$, and $R^6$ is other than hydrogen;

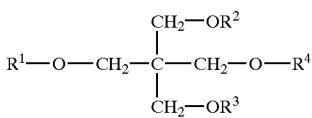

VIII wherein $R^1$, $R^2$, $R^3$, and $R^4$ are independently selected from the group consisting of hydrogen, alkanoyl having 2 to 6 carbons, hydroxy-substituted alkanoyl having 2 to 6 carbons, and acyloxy-substituted alkanoyl having 2 to 6 carbons, and wherein at least one of $R^1$, $R^2$, $R^3$, and $R^4$ is other than hydrogen.

In a more particular aspect, the novel compound has the structure:

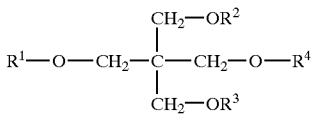

wherein $R^1$, $R^2$, $R^3$, and $R^4$ are independently selected from the group consisting of hydrogen, alkanoyl having 2 to 6 carbons, hydroxy-substituted alkanoyl having 2 to 6 carbons, and acyloxy-substituted alkanoyl having 2 to 6 carbons, and wherein at least one of $R^1$, $R^2$, $R^3$, and $R^4$ is other than hydrogen.

The liquid compositions of the invention can be used in any of the utilities or applications disclosed for HVLCM or LVLCM in U.S. Ser. No. 08/944,022, U.S. Ser. No. 478,450, and U.S. Ser. No. 08/474,337, now U.S. Pat. No. 5,747,058, the entire contents of each of which are hereby incorporated by reference.

BRIEF DESCRIPTION OF DRAWINGS

The invention can be better understood by reference to the following illustrative drawings, which are intended to illustrate and not to limit the scope thereof.

FIG. 1 is a graph showing the cumulative release profiles for bupivacaine from decaglycerol tetraoleate and from a 1,6-hexanediol lactate ε-hydroxycaproic acid according to the invention.

FIG. 2 is a graph showing the cumulative release profile for estradiol from a glycerol lactate glycolate according to the invention.

FIG. 3 is a graph showing the cumulative release profile for progesterone from a 1,6-hexanediol lactate glycolate according to the invention.

FIG. 4 is a graph showing the cumulative release profile for lysozyme from hexaglycerol dioleate and a glycerol lactate glycolate according to the invention.

DETAILED DESCRIPTION OF SPECIFIC EMBODIMENTS

Non-Water-Soluble High Viscosity Liquid Carrier Material

The high viscosity liquid carrier material should be selected that is non-polymeric, non-water soluble, and has a viscosity of at least 5,000 cP, (and optionally at least 10,000, 15,000; 20,000; 25,000 or even 50,000 cP) at 37° C. that does not crystallize neat under ambient or physiological conditions. The term "non-water soluble" refers to a material that is soluble in water to a degree of less than one percent by weight under ambient conditions. The term "nonpolymeric" refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "nonpolymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to about 20 etherified polyols in the alcohol moiety thereof, or 1 to about 10 glycerol moieties in the alcohol moiety thereof, are considered nonpolymeric as that term is used herein.

In a particular embodiment, the high viscosity liquid carrier material (HVLCM) decreases in viscosity, in some cases significantly, when mixed with a solvent to form a low viscosity liquid carrier material (LVLCM) that can be administered as a medical or surgical implant, graft, or film, or mixed with a biologically active substance for controlled delivery, or a combination thereof. The LVLCM/biologically active substance composition is typically easier to place in the body than a HVLCM/biologically active substance composition, because it flows more easily into and out of syringes or other implantation means. It also can easily be formulated as an emulsion. The LVLCM can have any desired viscosity. It has been found that a viscosity range for the LVLCM of less than approximately 6,000 cP, more particularly, less than approximately 4,000 cP, even more particularly, less than approximately 1,000 cP, and yet even more particularly less than 200 cP, is typically useful for in vivo applications.

The particular HVLCM used in the invention can be one or more of a variety of materials. Suitable materials include nonpolymeric esters or mixed esters of one or more carboxylic acids. In a particular embodiment, the ester is formed from carboxylic acids that are esterified with a polyol having from about 2 to about 20 hydroxy moieties, and which may include 1 to about 20 etherified polyols. Particularly suitable carboxylic acids for forming the acid moiety of the ester of the HVLCM include carboxylic acids having one or more hydroxy groups, e.g., those obtained by ring opening alcoholysis of lactones, or cyclic carbonates or by the alcoholysis of carboxylic acid anhydrides. Amino acids are also suitable for forming esters with the polyol. In a particular embodiment, the ester or mixed ester contains an alcohol moiety having one or more terminal hydroxy moieties that have been esterified with one or more carboxylic acids obtained by alcoholysis of a carboxylic acid anhydride, such as a cyclic anhydride.

Nonlimiting examples of suitable carboxylic acids that can be esterified to form the HVLCM of the invention include glycolic acid, lactic acid, ε-hydroxycaproic acid, serine, and any corresponding lactones or lactams, trimethylene carbonate, and dioxanone. The hydroxy-containing acids may themselves be further esterified through the reaction of their hydroxy moieties with additional carboxylic acid, which may be the same as or different from other carboxylic acid moieties in the material. Suitable lactones include, but are not limited to, glycolide, lactide, ε-caprolactone, butyrolactone, and valerolactone. Suitable carbonates include but are not limited to trimethylene carbonate and propylene carbonate.

The alcohol moiety of the ester or mixed ester may be derived from a polyhydroxy alcohol having from about 2 to about 20 hydroxy groups, and as indicated above, may be formed by etherifying 1 to 20 polyol molecules. Suitable alcohol moieties include those derived by removing one or more hydrogen atoms from: monofunctional $C_1$–$C_{20}$ alcohols, difunctional $C_1$–$C_{20}$ alcohols, trifinctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, the alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, fructose, sucrose, glucuronic acid, polyglycerol ethers containing from 1 to about 10 glycerol units, polyethylene glycols containing 1 to about 20 ethylene glycol units.

In particular embodiments of the invention, at least one of the carboxylic acid moieties of the esters or mixed esters of the invention comprise at least one oxy moiety In an even more particular embodiment, each of the carboxylic acid moieties comprise at least one oxy moiety.

In another particular embodiment, at least one of the carboxylic acid moieties of the esters or mixed esters of the invention contains 2 to 4 carbon atoms. In an even more particular embodiment, each of the carboxylic acid moieties of the esters or mixed esters of the invention contain 2 to 4 carbon atoms.

In another more particular embodiment of the invention, at least one of the carboxylic acid moieties of the ester or mixed ester of the invention has 2 to 4 carbon atoms and contains at least one oxy moiety. In another more particular embodiment of the invention, each of the carboxylic acid moieties of the ester or mixed ester of the invention has 2 to 4 carbon atoms and contains at least one oxy moiety.

In a particular embodiment, the invention includes compounds, compositions, and methods of use as described above, wherein the HVLCM has a structure selected from the group consisting of:

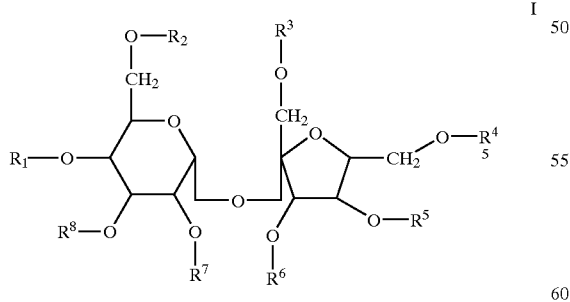

I wherein $R^1$, $R^2$, $R^3$, $R^4$, $R^5$, $R^6$, $R^7$, and $R^8$ are independently selected from the group consisting of hydrogen, alkanoyl, hydroxy-substituted alkanoyl, and acyloxy-substituted alkanoyl;

wherein at least three of $R^1$, $R^2$, $R^3$, $R^4$, $R^5$, $R^6$, $R^7$, and $R^8$ are other than hydrogen; and wherein when $R^1$, $R^2$, $R^3$, $R^4$, $R^5$, $R^6$, $R^7$, and $R^8$ are selected from the group consisting of acetyl and isobutyryl, at least three of $R^1$, $R^2$, $R^3$, $R^4$, $R^5$, $R^6$, $R^7$, and $R^8$ are acetyl;

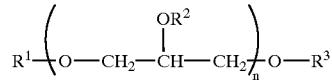

II wherein $R^1$, $R^2$, and $R^3$ are independently selected from the group consisting of hydrogen, alkanoyl, hydroxy-substituted alkanoyl, and acyloxy-substituted alkanoyl and wherein n is between 1 and 20;

III wherein n is an integer between 4 and 8, and $R^1$ and $R^2$ are independently selected from the group consisting of hydrogen, alkanoyl, hydroxy-substituted alkanoyl, and acyloxy-substituted alkanoyl;

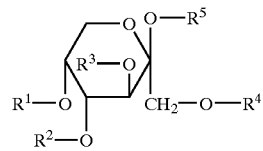

IV

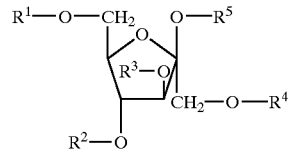

V wherein in formulae IV and V, $R^1$, $R^2$, $R^3$, $R^4$, and $R^5$ are independently selected from the group consisting of hydrogen, alkanoyl, hydroxy-substituted alkanoyl, and acyloxy-substituted alkanoyl;

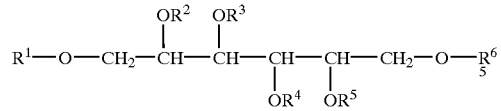

VI

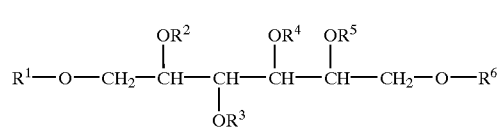

VII wherein in formulae VI and VII, $R^1$, $R^2$, $R^3$, $R^4$, $R^5$, and $R^6$ are independently selected from the group consisting of hydrogen, alkanoyl, hydroxy-substituted alkanoyl, and acyloxy-substituted alkanoyl;

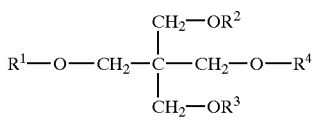

wherein R¹, R², R³, and R⁴ are independently selected from the group consisting of hydrogen, alkanoyl, hydroxy-substituted alkanoyl, and acyloxy-substituted alkanoyl.

In each of formulae I through VIII, one or more of the alkanoyl, hydroxy-substituted alkanoyl, and acyloxy-substituted alkanoyl groups may comprise alkanoyl moieties having 2 to 6 carbon atoms, including the carbonyl carbon. Moreover, in another more particular embodiment of the invention, each of formulae I through VIII comprise at least one hydroxy-substituted or acyloxy-substituted alkanoyl moiety. In an even more particular embodiment, at least one of these hydroxy-substituted or acyloxy-substituted alkanoyl moieties comprise alkanoyl moieties having 2 to 6 carbon atoms, including the carbonyl carbon.

The acyl groups forming the acyloxy substituents of the invention may be any moiety derived from a carboxylic acid in accordance with the commonly accepted definition of the term "acyl." More particularly, the acyl groups of the compositions of the invention may be of the form R⁹CO—, where R⁹ is optionally oxy-substituted alkyl of 2–6 carbon atoms. This oxy-substitution may take the form of hydroxy substitution, or substitution with additional acyl moieties. For example R⁹ may be an oligomer of oxy-substituted carboxylic acids, linked by ester bonding between the hydroxy of one acid and the carboxy of another acid. In a more particular example, R⁹ may comprise 1 to 5 lactide or glycolide units, where a lactide unit contains two lactic acid moieties esterified together and a glycolide unit contains two glycolic acid moieties esterified together. Alternatively, R⁹ may contain mixed lactide and glycolide units, or may contain mixed lactic acid and glycolic acid, without the presence of lactide or glycolide units.

Particular HVLCM materials include components according to formulae II or III, wherein R¹, R², and R³ are independently lactoyl, polylactoyl, ε-caproyl, hydroxyacetyl, or polyhydroxyacetyl, in particular, polylactoyl and ε-caproyl, or polylactoyl and polyhydroxyacetyl.

The use of relatively small chain (2 to 6 carbon atoms), oxy-substituted carboxylic acid moieties in the ester or mixed ester of the invention is advantageous. When these acid moieties are present in the form of oligomeric esters (i.e., a subsequent acid moiety joined to the previous acid moiety through esterification of the subsequent carboxy with the previous oxy), hydrolysis of the material is considerably easier than for oligomers made with more than 6 carbon atoms because the material is more hydrophilic. In general, for drug delivery it is desired that the HVLCM be water insoluble, but somewhat hydrophilic. In general, HVLCMs synthesized with more hydrophilic units (as determined by a higher O:C ratio) will be expected to absorb water more rapidly and degrade more quickly. For example, a HVLCM made by covalently linking 4 moles of glycolide to one mole of glycerol will be expected to absorb water more rapidly and degrade more quickly than a HVLCM made by covalently linking 2 moles of glycolide and 2 moles of lactide to one mole of glycerol. Similar increases can be expected for more flexible molecules and for more branched, spherical molecules based on free volume arguments. Use of flexible and branched molecules may also have the benefit of lowering the viscosity of the LVLCM. Using carboxylic acids and/or polyols of different chain length and using carboxylic acids having oxy-substitution allows a precise control of the degree of hydrophilicity and of the solubility of the resulting ester. These materials are sufficiently resistant to dissolution in vivo that they are able to provide a controlled release of bioactive substances into the body accompanied or followed by oxy bonds hydrolyzing in vivo.

In an even more particular embodiment, the invention excludes the acetate and isobutyrate ester of sucrose having a ratio of acetate to isobutyrate acid moieties of 2:6. However, sucrose acetate isobutyrate ester having a ratio of acetate to isobutyrate moieties of 2;6 is included within the scope of the invention for use in aerosol formulations, as well as for the delivery of lysozyme, paclitaxel, 5-fluorouracil, and antiretroviral drugs like AZT and ddC, as described and exemplified below. This material can be made according to the procedures described in U.S. Pat. No. 2,931,802.

In general, the HVLCM esters of the invention can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. The esterification reaction can be conducted simply by heating, although in some instances addition of a strong acid or strong base esterification catalyst may be used. Alternatively, an esterification catalyst such as stannous 2-ethylhexanoate can be used. The heated reaction mixture, with or without catalyst, is heated with stirring, then dried, e.g., under vacuum, to remove any unreacted starting materials, to produce a liquid product. Sucrose acetate isobutyrates can be made by following the procedures described in U.S. Pat. No. 2,931,802.

In this regard, the polyol can be viewed as an oligomerization initiator, in the sense that it provides a substrate for esterification of carboxylic acids, in particular, of oligomers of lactide, glycolide, or other esterified hydroxy-substituted carboxylic acids.

Solvents

As described above, in one embodiment of the invention, the HVLCM can be mixed with a viscosity lowering solvent to form a lower viscosity liquid carrier material (LVLCM), which can then be mixed with the biologically active substance to be delivered, prior to administration. These solvents can water soluble, non-water soluble, or water miscible, and can include, acetone, benzyl alcohol, benzyl benzoate, N-(betahydromethyl) lactamide, butylene glycol, caprolactam, caprolactone, corn oil, decylmethylsulfoxide, dimethyl ether, dimethyl sulfoxide, 1-dodecylazacycloheptan-2-one, ethanol, ethyl acetate, ethyl lactate, ethyl oleate, glycerol, glycofurol (tetraglycol), isopropyl myristate, methyl acetate, methyl ethyl ketone, N-methyl-2-pyrrolidone, MIGLYOLs (esters of caprylic and/or capric acids with glycerol or alkylene glycols, e.g., MIGLYOL 810 or 812 (caprylic/capric triglycerides), MIGLYOL 818 (caprylic/capric/linoleic triglyceride), MIGLYOL 829 (caprylic/capric/succinic triglyceride), MIGLYOL 840 (propylene glycol dicaprylate/caprate)), oleic acid, peanut oil, polyethylene glycol, propylene carbonate, 2-pyrrolidone, sesame oil, SOLKETAL ([±]-2,2-dimethyl-1,3-dioxolane-4-methanol), tetrahydrofi uran, TRANSCUTOL (diethylene glycol monoethyl ether, carbitol), triacetin, triethyl citrate, and combinations thereof. Additionally, if the composition is to be applied as an aerosol, e.g. for topical application, the solvent may be or may include one or more propellants, such as CFC propellants like trichlorofluoromethane and dichlorofluoromethane, non-CFC propellants like tetrafluoroethane (R-134a), 1,1,1,2,3,3,3-heptafluoropropane (R-227), dimethyl ether, propane, and butane. Particularly suitable solvents and/or propellants include benzyl benzoate, dimethyl sulfoxide, ethanol, ethyl lactate, glycerol, glycofurol (tetraglycol), N-methyl-2-pyrrolidone, MIGLYOL 810, polyethylene glycol, propylene carbonate, 2-pyrrolidone, and tetrafluoroethane.

When the composition is used as a LVLCM in conjunction with administration of a biologically active substance, it should contain a solvent that the HVLCM is soluble in. In certain instances, the substance to be delivered is also soluble in the solvent. The solvent should be non-toxic and otherwise biocompatible. Solvents that are toxic should not be used for pharmaceutical or agricultural purposes. The solvents used to inject the composition into animals should not cause significant tissue irritation or necrosis at the site of implantation, unless irritation or necrosis is the desired effect.

In one embodiment, the solvent should be at least water soluble, so that it will diffuse quickly into bodily fluids or other aqueous environment, causing the composition to coagulate or solidify. In another embodiment, the solvent is not completely miscible with water or bodily fluids so that diffusion of the solvent from the composition, and the corresponding increase in viscosity of the composition, are slowed.

When esters of 1,6-hexanediol or glycerol are used as the HVLCM, some possible solvents are ethanol, N-methylpyrrolidone, propylene carbonate, and PEG 400.

The solvent is typically added to the compositions in an amount in the range from about 1 percent to about 95 percent by weight, more particularly from about 5 to about 90 wt %, relative to the total weight of the composition. Even more particularly, the solvent is present in the composition in an amount in the range from about 10 percent to about 55 percent by weight. Other particular ranges include from about 10 percent to 50 percent by weight, and from about 10 to about 30 percent by weight.

A further embodiment involves the use of solvents that are not solvents for the HVLCM such that when combined with the HVLCM singularly or in combination with a solvent for the HVLCM, the resulting composition forms an emulsion. Such emulsions may contain the HVLCM in the dispersed phase such as in the case of SAIB/MIGLYOL mixtures that are emulsified in water or glycerol, or they may contain the HVLCM as a component of the continuous phase such as in the case of an aqueous solution that is emulsified in the HVLCM or a solution of the HVLCM in a water immiscible solvent.

Substance to be Delivered

When the HVLCM or LVLCM is to be used as a vehicle for delivery or controlled release of a substance to an animal or plant, this substance may be any substance that exhibits a desired property. In a particular embodiment, the substance is a biologically active substance.

The term "biologically active substance" as used herein refers to an inorganic or organic molecule including a drug, peptide, protein, carbohydrate (including monosaccharides, oligosacchandes, and polysaccharides), nucleoprotein, mucoprotein, lipoprotein, synthetic polypeptide or protein, or a small molecule linked to a protein, glycoprotein, steroid, nucleic acid (any form of DNA, including CDNA, or RNA, or a fragment thereof), nucleotide, nucleoside, oligonucleotides (including antisense oligonucleotides), gene, lipid, hormone, vitamin, including vitamin C and vitamin E, or combination thereof, that causes a biological effect when administered in vivo to an animal, including but not limited to birds and mammals, including humans.

Suitable proteins include, but are not limited to, human growth hormone, fibroblast growth factor (FGF), erythropoietin (EPO), platelet derived growth factor (PDGF), granulocyte colony stimulating factor (g-CSF), bovine somatotropin (BST), tumor necrosis factor (TNF), transforming growth factor-beta (TGF-Beta), interleukins, insulin, and interferon.

The term drug, as used herein, refers to any substance used internally or externally as a medicine for the treatment, cure, or prevention of a disease or disorder, and includes but is not limited to immunosuppressants, antioxidants, anesthetics, analgesics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers.

The term biologically active substance also includes agents such as insecticides, pesticides, fungicides, rodenticides, and plant nutrients and growth promoters.

In one embodiment, the composition functions as a vaccine and the substance to be delivered is an antigen. The antigen can be derived from a cell, bacteria, or virus particle, or portion thereof As defined herein, antigen may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell-mediated. In the event the material to which the immunogenic response is to be directed is poorly antigenic, it may be conjugated to a carrier such as albumin or to a hapten, using standard covalent binding techniques, for example, with one of the several commercially available reagent kits.

Examples of preferred antigens include viral proteins such as influenza proteins, human immunodeficiency virus (HIV) proteins, and hepatitis A, B, or C proteins, and bacterial proteins, lipopolysaccharides such as gram negative bacterial cell walls and *Neisseria gonorrhea* proteins, and parvovirus. The composition of the invention can also be used to elicit both mucosal and systemic immune responses by administration of the HVLCM of the invention, optionally with a solvent to decrease its viscosity as described above, in combination with an immunogenic material, in a vaccine that is administered to a mucosal surface, e.g., intranasally, intravaginally, or intrarectally. The immunogenic material may be any immunogenic agent whose delivery to mucosal tissue is desired. These immunogenic materials include antigens to vaccinate against viral, bacterial, protozoan, or fungal diseases, such as such as respiratory syncytial, parainfluenza viruses, *Hemophilus influenza, Bordetella pertussis, Neisseria gonorrhoeae, Streptococcus pneumoniae,* and *Plasmodium falciparum* or other diseases caused by pathogenic micro-organisms, antigens to vaccinate against diseases caused by macro-organisms such as helminthic pathogens, and antigens to vaccinate against allergens. In an even more particular aspect of this embodiment, the HVLCM or LVLCM is selected from formulae II through VIII above. Vaccines of this type can be prepared and administered by following the procedures described for SAIB in U.S. Provisional Application Serial No. 60/132,096, filed Apr. 30, 1999, the entire contents of which are hereby incorporated by reference.

In another embodiment, the composition functions as a controlled release composition for reproductive therapy, in humans or animals. For example, the HVLCM or LVLCM may be combined with gonadotropin releasing hormone or its analogs or agonists. In a particular aspect of this embodiment, the HVLCM or LVLCM is not SAIB having an acetate to butyrate ratio of 2:6. In an even more particular aspect of this embodiment, the HVLCM or LVLCM is selected from formulae II through VIII above. These compositions can be prepared and administered by following the procedures described for SAIB in U.S. Ser. No. 09/001,123, filed Dec. 30, 1997, the entire contents of which are hereby incorporated by reference.

Non-limiting examples of pharmacological materials include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; anti-allergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, diphtheria toxoid, tetanus toxoid, pigeon pox, whooping cough, influenzae rabies, mumps, measles, poliomyelitic, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; anesthetics, such as novicaine and bupivacaine; androgenic steroids such as methyl-testosterone and fluorymesterone; estrogens such as estrone, 17-fl-estradiol, ethinyl estradiol, and diethyl stilbestrol; progestational agents such as progesterone, megestrol, melengestrol, chiormadinone, ethisterone, norethynodrel, 19-norprogesterone, norethindrone, medroxyprogesterone and 17-0-hydroxy-progesterone; humoral agents such as the Prostaglandins, for example PGE1, PGE2 and PGF2; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins, natural and synthetic bioactive peptides and proteins, including growth factors, cell adhesion factors, cytokines, and biological response modifiers.

The active compound is included in the composition in an amount sufficient to deliver to the host animal or plant an effective amount to achieve a desired effect. The amount of drug or biologically active agent incorporated into the composition depends upon the desired release profile, the concentration of drug required for a biological effect, and the desired period of release of the drug.

The concentration of active compound in the composition will also depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The composition may be administered in one dosage, or may be divided into a number of smaller doses to be administered at varying intervals of time.

The biologically active substance is typically present in the composition in the range from about 0.1 percent to about 20 percent by weight, more particularly fom about 0.5 percent to about 20 percent by weight relative to the total weight of the composition, and more typically, between approximately 1 percent to about 15 percent by weight, and more. Another preferred range is from about 2 percent to about 10 percent by weight. For very active agents, such as growth factors, preferred ranges are less than 1% by weight, and less than 0.0001%.

Both soluble and insoluble substances can be distributed in the HVLCM or LVLCM for controlled delivery. Moreover, the formulations containing biologically active substances and an HVLCM or LVLCM may be further formulated with polymeric excipients to provide a drug delivery matrix with modified properties, for example a faster or slower degradation rate. The resulting composition may be formed into microspheres, or into a macroscopic implant, or other geometries and sizes according to techniques known in the art. Alternatively, a pre-formed microsphere or implant with a biologically active substances incorporated therein can be combined with the HVLCM or LVLCM, for example as an injection vehicle. Here the HVLCM or LVLCM will form an secondary barrier to provide enhanced drug delivery. The HVLCM or LVLCM phase may or may not contain other biologically active substances, according to the specific biological requirement. These other biologically active substances may be any of those described above, provided that the biologically active substance must be suitable for incorporation into microspheres or implants according to techniques known in the art.

Additives

A variety of additives can optionally be added to the HVLCM or LVLCM to modify the properties of the material as desired, and in particular to modify the release properties of the composition with respect to biologically active substances contained therein. The additives can be present in any amount which is sufficient to impart the desired properties to the composition. The amount of additive used will in general be a function of the nature of the additive and the effect to be achieved, and can be easily determined by the routineer. Suitable additives are described in U.S. Pat. No. 5,747,058, the entire contents of which are hereby incorporated by reference. More particularly, suitable additives include water, biodegradable polymers, non-biodegradable polymers, natural oils, synthetic oils, carbohydrates or carbohydrate derivatives, inorganic salts, BSA (bovine serum albumin), surfactants, organic compounds, such as sugars, and organic salts, such as sodium citrate. Some of these classes of additives are described in more detail below. In general, the less water soluble, i.e., the more lipophilic, the additive, the more it will decrease the rate of release of the substrate, compared to the same composition without the additive. In addition, it may be desirable to include additives that increase properties such as the strength or the porosity of the composition.

The addition of additives can also be used to lengthen the delivery time for the active ingredient, making the composition suitable for treatment of disorders or conditions responsive to longer term administration. Suitable additives in this regard include those disclosed in U.S. Pat. No. 5,747,058. In particular, suitable additives for this purpose include polymeric additives, such as cellulosic polymers and biodegradable polymers. Suitable cellulosic polymers include cellulose acetates, cellulose ethers, and cellulose acetate butyrates. Suitable biodegradable polymers include polylactones, polyanhydrides, and polyorthoesters, in particular, polylactic acid, polyglycolic acid, polycaprolactone, and copolymers thereof.

When present, the additive is typically present in the compositions in an amount in the range from about 0.01 percent to about 20 percent by weight, more particularly from about 0.1 percent to about 20 percent by weight, relative to the total weight of the composition, and more typically, is present in the composition in an amount in the range from about 1, 2, or 5 percent to about 10 percent by weight. Certain additives, such as buffers, are only present in small amounts in the composition.

The following categories are nonlimiting examples of classes of additives that can be employed in the composition.

Given the disclosure herein and the objects to be achieved, one of skill in the art will easily know how to select other additives to achieve a desired purpose. All of these embodiments are considered to fall within the disclosed invention.

A. Biodegradable Polymers

One category of additives are biodegradable polymers and oligomers. The polymers can be used to alter the release profile of the substance to be delivered, to add integrity to the composition, or to otherwise modify the properties of the composition. Non-limiting examples of suitable biodegradable polymers and oligomers include: poly(lactide), poly(lactide-co-glycolide), poly(glycolide), poly(caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyethylenes, polyhydroxybutyrates, polyhydroxyvalerates, polyalkylene oxalates, polyalkylene succinates, poly(malic acid), chitin, chitosan, and copolymers, terpolymers, oxidized cellulose, or combinations or mixtures of the above materials.

Examples of poly(a-hydroxy acid)s include poly(glycolic acid), poly(DL-lactic acid) and poly(L-lactic acid), and their copolymers. Examples of polylactones include poly(ε-caprolactone), poly(δ-valerolactone) and poly(ganmmabutyrolactone).

B. Non-biodegradable Polymers

Another additive for use with the present compositions are non-biodegradable polymers. Non-limiting examples of nonerodible polymers which can be used as additives include: polyacrylates, ethylene-vinyl acetate polymers, cellulose and cellulose derivatives, acyl substituted cellulose acetates and derivatives thereof, non-erodible polyethylenes, polystyrenes, polyvinyl chloride, polyvinyl fluoride, poly-vinyl (imidazole), chlorosulphonated polyolefins, polyethylene oxide, and polyethylene.

Preferred non-biodegradable polymers include polyvinyl pyrrolidone, ethylene vinylacetate, polyethylene glycol, cellulose acetate butyrate ("CAB") and cellulose acetate propionate ("CAP").

C. Oils and Fats

A further class of additives which can be used in the present compositions are natural and synthetic oils and fats. Oils derived from animals or from plant seeds of nuts typically include glycerides of the fatty acids, chiefly oleic, palmitic, stearic, and linoleic. As a rule the more hydrogen the molecule contains the thicker the oil becomes.

Non-limiting examples of suitable natural and synthetic oils include vegetable oil, peanut oil, medium chain triglycerides, soybean oil, almond oil, olive oil, sesame oil, peanut oil, fennel oil, camellia oil, corn oil, castor oil, cotton seed oil, and soybean oil, either crude or refined, and medium chain fatty acid triglycerides.

Fats are typically glyceryl esters of higher fatty acids such as stearic and palmitic. Such esters and their mixtures are solids at room temperatures and exhibit crystalline structure. Lard and tallow are examples. In general oils and fats increase the hydrophobicity of the HVLCM, slowing degradation and water uptake.

D. Carbohydrates and Carbohydrate Derivatives

Another class of additives which can be used in the present compositions are carbohydrates and carbohydrate derivatives. Non-limiting examples of these compounds include monosaccarides (simple sugars such as fructose and its isomer glucose (dextrose); disaccharides such as sucrose, maltose, cellobiose, and lactose; and polysaccharides.

Uses of the LVLCM and HVLCM Compositions

The composition described herein can be administered to the host through a variety of methods which can vary depending on the result to be achieved. When the host is an animal, such as a human, the composition can be administered, for example, topically, systematically (for example, mucosally (orally, rectally, vaginally, or nasally), parenterally (intravenously, subcutaneously, intramuscularly, or intraperitoneally), or through the pulmonary system, in an appropriate carrier, if desired. When the composition is used for administration to humans or animals, or used for agricultural purposes, it can be applied via injection, pouring, spray dip, aerosol, or coating applicator. Aerosols or mists of the composition can be administered using an aerosol propellant, e.g., for topical administration, or using a suitable nebulizer, e.g., for pulmonary, nasal, or oral mucosal administration.

Preferably, for pharmaceutical or veterinary purposes, the present compositions are administered as liquids via injection, or in an aerosol, paste or emulsion. When administered via injection as a LVLCM, if a water-soluble solvent has been used in the composition, the solvent leaches into the aqueous fluid of the host, forming a highly viscous depot for the controlled delivery of substances or a coating for tissue that can prevent or minimize adhesions. As explained above, the use of a water soluble solvent in making the LVLCM significantly decreases the leaching time. When used in an aerosol or in an emulsion, the small amount of solvent in the solution evaporates upon application allowing the LVLCM to set-up as an HVLCM. Formation of aerosols and emulsions can be accomplished using techniques known to those skilled in the art. See, for example, Ansel, H. C. et al., *Pharmaceutical Dosage Forms and Drug Delivery Systems*, sixth ed., 1995.

The compositions can be used to form protective tissue coatings, and in particular, can be used to prevent the formation of surgical adhesions. The HVLCM can adhere to the surrounding tissue or bone, and can thus be injected subdermally like collagen to build up tissue or to fill in defects. It can also be injected into wounds including burn wounds to prevent the formation of deep scars. The degradation time of the HVLCM can be modulated, for example, by using a polymer as an additive to the HVLCM. Then the implant formed by the HVLCM will slowly biodegrade within the body and allow natural tissue to grow and replace the implant as it disappears. These compositions may optionally contain biologically active substances including but not limited to, anesthetics, analgesics, antibiotics, and antinflammatories.

As indicated above, the HVLCM and LVLCM materials of the invention can be used not only for the controlled release and delivery of substances, such as bioactive substances, to plants or animals, but also as medical or surgical devices, as described in U.S. Ser. No. 08/944022, the entire contents of which are incorporated by reference.

Device utilities for the compositions of the invention include, but are not limited to blocking surgical adhesions, void filling, guided tissue regeneration, inducing hemostasis, tissue adhesive, scaffolding, and wound dressing. Each of these applications can optionally include release of a biologically active substance, or drug delivery. For example, the nonpolymeric ester or mixed ester composition as a wound dressing readily accommodates various growth factors to accelerate healing of the wound. In general, for these utilities a composition can be used having the non-polymeric non-water-soluble liquid carrier material present in an amount from about 99.5 percent to about 25 percent by weight, relative to the total weight of the composition. These compositions can be diluted with a solvent, including but not limited to one or more of ethanol, dimethylsulfoxide, ethyl lactate, ethyl acetate, benzyl alcohol, triacetin, 2-pyrrolidone, N-methylpyrrolidone, propylene carbonate, glycofurol, capric/caprylic triglycerides, benzyl benzoate, ethyl oleate, isopropyl myristate, triethyl citrate, and any aerosol propellant, to a concentration of the non-polymeric non-water-soluble liquid carrier material of about 10 to about 90% by weight, calculated based on the total weight of the composition, to obtain an implantable or sprayable composition.

For blocking surgical adhesions, a sprayed-on or painted-on film to block adhesion of similar or dissimilar organs is suitable. The nonpolymeric ester or mixed ester composition is formulated in any of a variety of solvents, including ethanol, ethyl lactate, N-methyl-2-pyrrolidone, or any common aerosol propellant, dimethyl ether, or any propellant, with or without an additive, and can be applied as an aerosol spray. The resulting film may effect adhesion, cohesion, degradation or porosity, or a combination thereto.

For void filling, the nonpolymeric ester or mixed ester composition is typically suitable like collagen for cosmetic repair. In related applications, the nonpolymeric ester or mixed ester composition is useful for holding bone chips together in a fracture, and may optionally include an anesthetic, antibiotic, or growth factor for targeted delivery.

Guided tissue regeneration is another application, such as periodontal repair to block epithelial migration. Advantageously, the compositions of the present invention are applied from solution. Typical drugs incorporated into these compositions for guided tissue regeneration include but are not limited to a variety of growth factors and cell reattachment factors.

Hemostasis or stopping blood flow is another utility, typically in a surgical setting. The compositions of the present invention are biodegradable. Suitable additives include, but are not limited to polyvinyl alcohol, polyethylene glycol or carboxymethyl cellulose. Suitable solvents include ethyl lactate and propylene carbonate.

A spray-on or paint-on formulation of the nonpolymeric ester or mixed ester composition is suitable as a tissue adhesive for wound closure, either as a primary sealant or in conjunction with sutures or staples. Suitable additives include but are not limited to carboxymethylcellulose or polyvinylpyrrolidone. Suitable solvents include but are not limited to propylene carbonate, ethyl lactate, glycofural, dimethylsulfoxide, 2-pyrrolidone, N-methyl-2-pyrrolidone, and ethanol. Biologically active substances incorporated into these compositions for tissue adhesion include but are not limited to antibiotics, anti-inflammatory compounds, analgesics, anesthetics and growth factors.

Scaffolding is another device utility for the compositions of the present invention, and is particularly adaptive to new tissue growth. A typical formulation includes polyvinylpyrrolidone and tricalcium phosphate. The scaffolding provides a matrix suitable for the attachment and growth of bone or nerve cells. Biologically active substances incorporated into these compositions for scaffolding include but are not limited to growth factors.

Another application of the compositions of the present invention is a wound dressing, with or without appropriate drugs incorporated therein. The wound dressing functions to protect the wound and accelerate the healing process. In one typical application, the nonpolymeric ester or mixed ester composition is applied as an aerosol spray. Biologically active substances incorporated into these compositions in wound dressing include but are not limited to antibiotics, such as amikacin, anti-inflammatory compounds, analgesics, anesthetics, or growth factors such as fibroblast growth factors.

Whether the compositions of the invention are used as for controlled release delivery of biologically active substances, or as devices or implants, the compositions can have very high viscosities. As described above, the HVLCM materials have a viscosity at 37° C. of at least 5,000 cP. In a more particular embodiment, the HVLCM materials have viscosities above 10,000 cP, more particularly above 15,000 cP, even more particularly above 20,000, 25,000, or 50,000 cP at 37° C.

EXAMPLE 1

High Viscosity Liquids of DL-Lactide/ε-Caprolactone 75/25 Initial Mole Concentration, Reacted with 1,6-Hexanediol A clean, one liter glass reaction flask was fitted with a stainless steel mechanical stirrer rinsed with acetone, and dried for 3 hours under 0.5 mm Hg vacuum, while immersed in a 150° C. oil bath. The reaction vessel was removed from the bath, allowed to cool, then charged with 197.5 grams (1.37 mol) of DL-Lactide, 52.5 grams (0.46 mol) of ε-Caprolactone, and 40 grams (0.34 mol) of 1,6-Hexanediol. Following addition, the reaction flask was purged 5 times with nitrogen, and immersed in the oil bath at 150° C. The mixture was stirred slowly after a majority appeared to have been melted to facilitate phase change. After all contents had melted, 1.28 mL (210 µmol) of a 0.164M stannous 2-ethylhexanoate solution in toluene was added. Stirring continued to disperse the catalyst for a period of approximately 1 hour. The solution was maintained, without stirring, for 18 hrs. at 150° C. The resulting compound was then dried under vacuum (<0.5 mm Hg) at 150° C. for a period of 4–5 hours to remove any unreacted starting materials, with slow stir speed applied. The resulting product had an inherent viscosity of 0.049 dL/g in $CHCl_3$ at 30° C.

EXAMPLE 2

High Viscosity Liquid of DL-Lactide/Glycolide at 75/25 Initial Mole Concentration, Reacted with 1,6-Hexanediol The procedure detailed in Example 1 was used to prepare a material using 247.13 g (1.71 mol) DL-Lactide, 62.87 g (0.54 mol) Glycolide, and 49.6 g (0.42 mol) 1,6-Hexanediol. Following initial melting, 1.84 mL (260 µmol) of a 0.141M stannous 2-ethylhexanoate solution in toluene was added. The resulting product had an inherent viscosity of 0.058 dL/g in $CHCl_3$ at 30° C. The material was a liquid at room temperature.

EXAMPLE 3

High Viscosity Liquid of DL-Lactide/ε-Caprolactone at 75/25 Initial Mole Concentration, Reacted with Glycerol The procedure described in Example 1 was used to prepare a material using 198.14 g (1.37 mol) DL-Lactide, 54.8 g (0.47 mol) ε-caprolactone, and 40 g (0.43 mol) Glycerol. Following initial melting, 1.36 mL (210 µmol) of a 0.154M stannous 2-ethylhexanoate solution in toluene was added. The resulting product had an inherent viscosity of 0,038 dL/g in $CHCl_3$ at 30° C. The product was a liquid at room temperature.

EXAMPLE 4

High Viscosity Liquid of DL-Lactide/Glycolide at 75/25 Initial Mole Concentration, Reacted with Glycerol The procedure described in Example 1 was used to prepare a compound using 247.33 g (1.72 mol) DL-Lactide, 62.87 g (0.54 mol) Glycolide, and 50.0 g (0.54 mol) Glycerol. Following initial melting, 1.46 mL (260 µmol) of a 0.179M stannous 2-ethylhexanoate solution in toluene was added. The resulting product had an inherent viscosity of 0.028 dL/g in $CHCl_3$ at 30° C. The material was a liquid at room temperature.

EXAMPLE 5

High Viscosity Liquid of Glycolide Reacted with Glycerol

A clean, one liter glass reaction flask was fitted with a stainless steel mechanical stirrer rinsed with acetone, and dried for 3 hours under 0.5 mm Hg vacuum, while immersed in a 150° C. oil bath. The reaction vessel was removed from the bath, allowed to cool, then charged with 174 grams (1.5 mol) of glycolide and 92 grams (1.0 mol) of glycerol. Following addition, the reaction flask was purged 5 times with nitrogen, and immersed in the oil bath at 150° C. The mixture was stirred slowly to facilitate phase change after a majority of the mixture appeared to have been melted. After all contents had melted, 1.28 mL (210 µmol) of a 0.164M stannous 2-ethylhexanoate solution in toluene was added. Stirring was continued to disperse the catalyst for a period of approximately 1 hour. The solution was maintained, without stirring, for 18 hrs. at 150° C. The resulting compound was then dried under vacuum (<0.5 mm Hg) at 150° C. for a period of 4–5 hours with slow stir speed applied to remove any unreacted starting materials.

EXAMPLE 6

High Viscosity Liquid of ε-Caprolactone Reacted with 1-Dodecanol

The procedure described in Example 5 was used to prepare a material using 513 gms (4.5 mol) ε-caprolactone and 93 g (0.5 mol) 1-dodecanol. Following addition of reagents, 1.36 mL (210 µmol) of a 0.154M stannous 2-ethylhexanoate solution in toluene was added. The reaction proceeded as described in Example 5 and was purified as described therein.

Methods of using the compositions of the invention are exemplified below.

EXAMPLE A

CAPROL 10G40 (decaglycerol tetraoleate) was dissolved in benzyl benzoate at a weight ratio of 50:50. Bupivacaine was dissolved in this mixture at a concentration of 8.75 wt %. Drops weighing approximately 100 mg were precipitated into a test tube containing 40 mL of buffer. Samples of the buffer were removed at specified time points and replaced with fresh buffer. The samples were analyzed by UV-vis spectrophotometry at 265 nm to determine the concentration of bupivacaine in each buffer sample. At 4 hours, less than 7.5 wt % of the bupivacaine in the drop had been released to the buffer. At 48 hours, around 24.0 wt % of the bupivacaine had been released. The cumulative release profile is shown in FIG. 1.

EXAMPLE B

The 1,6-hexanediol lactate ε-hydroxycaproic acid produced in Example 1 was dissolved in N-methylpyrrolidone at a weight ratio of 70:30. 10 wt % bupivacaine base was then added to this mixture and dissolved. Drops weighing approximately 100 mg were precipitated into 40 mL buffer. Samples of buffer were removed at specified times and replaced with fresh buffer. Buffer samples were analyzed by UV-vis spectrophotometry at 265 nm to determine the concentration of bupivacaine in each buffer sample. At 4 hours, around 4.1 wt % of the bupivacaine contained in the precipitated drop had been released. At 24 hours, around 8.6 wt % of the bupivacaine had been released. The cumulative release profile is shown in FIG. 1.

EXAMPLE C

The glycerol lactate glycolate prepared according to Example 4 was dissolved in ethanol at a weight ratio of 70:30. 10 wt % estradiol was then added to this mixture as a suspension. The formulation was homogenized prior to testing to ensure adequate mixing. Drops of this formulation were injected into a test tube containing buffer. The glycerol lactate glycolate precipitated, forming a depot from which the estradiol was slowly released. Samples of the buffer were removed at specified times and replaced with fresh buffer. The buffer samples removed from each test tube were analyzed by UV-vis spectrophotometry at 280 nm to determine the estradiol concentration in each sample. The assayed concentration was used to calculate the percent of estradiol released from the drop. FIG. 2 shows a cumulative release profile for estradiol.

EXAMPLE D

The 1,6-hexanediol lactate glycolate prepared according to Example 2 was dissolved in propylene carbonate at a weight ratio of 80:20. 10 wt % of progesterone was incorporated as a suspension into this mixture. The formulation was homogenized prior to testing to ensure adequate mixing. The resulting formulation was analyzed to determine its in vitro dissolution profile. Drops of the formulation were injected into a test tube containing buffer. The 1,6-hexanediol lactate glycolate precipitated, forming a depot from which the progesterone was slowly released. Samples of the buffer were removed at specified times and replaced with fresh buffer. The buffer samples were analyzed by UV-vis spectrophotometry at 244 nm to determine drug concentration in each sample. The assayed concentration was used to calculate the percentage of progesterone that had been released from the drop. The cumulative release profile is shown in FIG. 3.

EXAMPLE E

The glycerol lactate ε-hydroxycaproic acid prepared according to Example 3 was dissolved in polyethylene glycol (PEG) 400 at a weight ratio of 36:64. Lysozyme was ground with a mortar and pestle and the resulting powder was incorporated into the mixture as a suspension at a concentration of 10 wt %. The formulation was mixed thoroughly with a spatula. Samples of the formulation, approximately 500 μL in volume, were injected into three test tubes each containing 10 mL of buffer. Aliquots of buffer (8 mL) were removed at specified times and replaced with fresh buffer. Each sample of buffer containing lysozyme was analyzed with a micro BCA protein assay reagent kit to determine protein content in the dissolution sample. The assayed lysozyme concentration was used to calculate the percent of lysozyme that had been released from the drop. The cumulative release profile is shown in FIG. 4.

EXAMPLE F

CAPROL 6G20 (hexaglycerol dioleate) was dissolved in benzyl benzoate at a weight ratio of 25:75. Lysozyme was ground with a mortar and pestle and the resulting powder was incorporated into the mixture as a suspension at a concentration of 10 wt %. The formulation was mixed thoroughly with a spatula. Samples of the formulation, approximately 500 μL in volume, were injected into three test tubes each containing 10 mL of buffer. Aliquots of buffer (8 mL) were removed at specified times and replaced with fresh buffer. Each sample of buffer containing lysozyme was analyzed with a micro BCA protein assay reagent kit to determine protein content in the dissolution sample. The assayed lysozyme concentration was used to calculate the percent of lysozyme that had been released from the drop. The cumulative release profile is shown in FIG. 4.

EXAMPLE G

Two solutions were prepared in which 1,6-hexanediol lactate ε-hydroxycaproic acid (prepared according to Example 1) and 1,6-hexanediol lactate glycolate (prepared according to Example 2) were dissolved in polyethylene glycol (PEG) 400 at weight ratios of 34:66 and 33:67, respectively. A drop of each formulation was injected into a test tube containing deionized water, and the 1,6-hexanediol lactate 6-hydroxycaproic acid and 1,6-hexanediol lactate glycolate were precipitated at the bottom of the test tubes. The drops retained their shapes for longer than one week.

EXAMPLE H

The formulations listed in the Table below were prepared using the esters prepared in Examples 1 through 4. In each case, the mixture resulted in a homogeneous solution.

| Ester | Solvent | Ester:Solvent Wt Ratio |
|---|---|---|
| 1,6-hexanediol lactate glycolate | Ethanol | 80:20 |
| 1,6-hexanediol lactate ε-hydroxycaproic acid | Ethanol | 80:20 |
| glycerol lactate ε-hydroxycaproic acid | Ethanol | 80:20 |
| glycerol lactate glycolate | Ethanol | 80:20 |
| 1,6-hexanediol lactate glycolate | Propylene carbonate | 80:20 |
| 1,6-hexanediol lactate ε-hydroxycaproic acid | Propylene carbonate | 80:20 |
| glycerol lactate ε-hydroxycaproic acid | Propylene carbonate | 80:20 |
| glycerol lactate glycolate | Propylene carbonate | 80:20 |
| 1,6-hexanediol lactate glycolate | Polyethylene glycol (PEG) 400 | 36:64 |
| 1,6-hexanediol lactate ε-hydroxycaproic acid | Polyethylene glycol (PEG) 400 | 34:66 |
| glycerol lactate ε-hydroxycaproic acid | Polyethylene glycol (PEG) 400 | 33:67 |
| glycerol lactate glycolate | Polyethylene glycol (PEG) 400 | 37:63 |
| 1,6-hexanediol lactate glycolate | N-methyl-2-pyrrolidone | 80:20 |
| 1,6-hexanediol lactate ε-hydroxycaproic acid | N-methyl-2-pyrrolidone | 80:20 |
| glycerol lactate ε-hydroxycaproic acid | N-methyl-2-pyrrolidone | 80:20 |
| glycerol lactate glycolate | N-methyl-2-pyrrolidone | 80:20 |
| 1,6-hexanediol lactate glycolate | Benzyl benzoate | 70:30 |
| 1,6-hexanediol lactate glycolate | Glycofurol | 70:30 |
| 1,6-hexanediol lactate glycolate | Dimethyl sulfoxide | 70:30 |
| 1,6-hexanediol lactate ε-hydroxycaproic acid | Propylene glycol | 50:50 |
| 1,6-hexanediol lactate ε-hydroxycaproic acid | Benzyl benzoate | 70:30 |
| 1,6-hexanediol lactate ε-hydroxycaproic acid | Glycofurol | 70:30 |
| 1,6-hexanediol lactate ε-hydroxycaproic acid | Dimethyl sulfoxide | 70:30 |
| glycerol lactate ε-hydroxycaproic acid | Propylene glycol | 50:50 |
| glycerol lactate ε-hydroxycaproic acid | Benzyl benzoate | 70:30 |
| glycerol lactate ε-hydroxycaproic acid | Glycofurol | 70:30 |
| glycerol lactate ε-hydroxycaproic acid | Dimethyl sulfoxide | 70:30 |
| glycerol lactate glycolate | Propylene glycol | 50:50 |
| glycerol lactate glycolate | Glycofurol | 70:30 |
| glycerol lactate glycolate | Dimethyl sulfoxide | 70:30 |

-continued

| Ester | Solvent | Ester:Solvent Wt Ratio |
|---|---|---|
| glycerol lactate glycolate, acid end | Ethanol | 70:30 |
| glycerol lactate glycolate, acid end | Propylene carbonate | 70:30 |
| glycerol lactate glycolate, acid end | N-methyl-2-pyrrolidone | 70:30 |
| glycerol lactate glycolate, acid end | Propylene glycol | 50:50 |
| glycerol lactate glycolate, acid end | Glycofurol | 70:30 |
| glycerol lactate glycolate, acid end | Dimethyl sulfoxide | 70:30 |

EXAMPLE I 5.33 g of a 10 wt % solution of bupivacaine in a composition containing 70:30 SAIB/NMP, prepared as described in U.S. Pat. No. 5,747,058, was added to an aerosol container. 14.32 g of propellant R-134a (1,1,1,2-tetrafluoroethane) was added. The mixture formed a solution that was easily sprayed with no bubbling or foaming.

EXAMPLE J 5.44 g of a 10 wt % solution of bupivacaine in a composition containing 70:30 SAIB/NMP, prepared as described in U.S. Pat. No. 5,747,058, was added to an aerosol container. 16.55 g. of propellant R-134a (1,1,1,2-tetrafluoroethane) was added. The mixture formed a solution that was easily sprayed with no bubbling or foaming.

EXAMPLE K 0.87 g of bupivacaine base was added to an aerosol container. 8.47 g of an SAIB/propylene carbonate solution (70:30) containing 2.5 wt % of a biodegradable polymer (65:35 DLPLG) was added to the container. 0.98 g of ethanol was added to help the drug dissolve. Once dissolved, approximately 16 g of propellant R-134a (1,1,1,2-tetrafluoroethane) was added. The mixture formed a solution that was easily sprayed with no bubbling or foaming.

EXAMPLE L

SAIB was dissolved in propellants 134a (1,1,1,2-tetrafluoroethane) and 227 (1,1,1,2,3,3,3-heptafluoropropane) at levels of 5 and 10 wt %. Clear solutions were formed.

EXAMPLE M

An additional example was conducted to evaluate a novel controlled-release system, which uses a high-viscosity compound, sucrose acetate isobutyrate (SAIB), for use in providing sustained release of lysozyme. A small amount of solvent converts SAIB to an easily injectable liquid. Once injected, the solvent dissipates forming a high viscosity, biodegradable implant. Release profiles can be altered with different solvents and additives.

Ground lysozyme (10 wt %) was suspended in SAIB/solvent mixtures including the solvents ethyl lactate, N-methyl-2-pyrrolidone (NMP), MIGLYOL 810, and benzyl benzoate. Three poly (DL-lactide-co-glycolide) polymers with either acid, ester, or PEG end groups were evaluated as additives. To determine release rates, drops of formulation were injected into test tubes with pH 6.24 buffer and then incubated in a shaker at 37° C. At certain times, aliquots of buffer were removed and replaced with fresh buffer. Lysozyme concentration in buffer was determined by the BCA protein assay. Protein activity was determined with an enzymatic assay measuring cell lysis of a suspension of *Micrococcus lysodeikticus* spectrophotometrically. Decrease in absorbance at 450 nm was recorded as a function of time, which is directly related to active lysozyme concentration.

At 6 hours, release ranged from 1.3 wt % for the 70:30 SAIB/NMP formulation (110.3±5.0% activity) to 4.5 wt % for the 40:60 SAIB/ethyl lactate formulation (107.6±6.1% activity). The percent released at 7 days ranged from 46.7% for 40:60 SAIB/ethyl lactate (88.9±6.8% activity) to 96.4% for 70:30 SAIB/MIGLYOL (107.6+7.0% activity). Addition of 0.5 wt % of each of the three polymers to an SAIB/NMP formulation did not significantly affect the release profile.

These results demonstrate that the SAIB/solvent delivery system described above is capable of providing sustained release of proteins in an active state, and that the rate of release can be modulated to provide a range of release profiles.

EXAMPLE N

An additional example was conducted to evaluate the effects of formulation variables on release of chemotherapeutic agents—paclitaxel and 5-fluorouracil (5-FU)—from formulations based on an SAIB delivery system. It will be understood from the description above that the SAIB delivery system uses sucrose acetate isobutyrate (SAIB), a fully-esterified, water-insoluble sucrose derivative, as an ekcipient. It can be formulated as a low- to medium-viscosity liquid by the addition of small amounts of solvents such as ethanol, MIGLYOL, ethyl lactate, propylene carbonate, or DMSO, resulting in an easily injectable formulation.

Solutions of SAIB in the appropriate solvent were prepared with and without the incorporation of an additive. The active was weighed into a test tube and the SAIB/mixture was added and mixed thoroughly to yield a solution or suspension at the desired drug loading. Single drops of the mixture were precipitated into buffer by injection with standard syringes and needles. Samples were maintained at 37° C. in a shaker, sampled periodically, and analyzed by UV-vis spectrophotometry for active release. Paclitaxel and 5-FU samples were analyzed at 232 nm and 266 nm, respectively.

The effect of drug loading was evaluated for paclitaxel. Drug loadings of 5, 25, and 50 mg/mL were compared. After 7 days, the cumulative release for these three drug loading were 106.4%, 85.9%, and 33.8%, respectively. The effect of surfactant additives was also evaluated. A 25 mg/mL paclitaxel formulation and a 10 mg/mL 5-FU formulation, both in 85:15 SAIB/EtOH, were made and 5 wt % Cremophore® EL was added. The addition of this surfactant increased the rate of release for both formulations. The percent released from the paclitaxel formulation increased from 56.0% to 77.0% after two days in vitro. Likewise, the percent released from the 5-FU formulation increased from 80.6% to 106.0% after two days. A second surfactant, Pluronic®L-101, was added to a 10 mg/mL 5-FU in 85:15 SAIB/EtOH formulation. This surfactant also increased the amount released from 80.6% to 102.0% after two days.

The rate of release of drugs such as paclitaxel and 5-fluorouracil from the SAIB delivery system can be modulated by formulation variables including drug loading and surfactant type. Also, the duration of release of these drugs from this system can be varied from a few hours to several days with the shorter duration seen at the lower drug loading and with the addition of a surfactant.

EXAMPLE O

Another example was conducted to evaluate the potential of the SAIB delivery system to provide extended release following oral administration of antiretroviral drugs used for treating HIV infections. As indicated above, the SAIB delivery system uses sucrose acetate isobutyrate (SAIB), a fully-esterified, water-insoluble sucrose derivative, as an excipient.

Zidovudine (AZT) and dideoxycytodine (ddC) suspensions were prepared by mixing drug with SAIB/solvent solutions with and without a cellulosic coexcipient. Approximately 1 g of each formulation was filled into soft gelatin capsules, which were heat sealed. Dissolution profiles were determined using Apparatus 2, Method B (USP XXIII) at a paddle speed of 50 rpm. Individual gelcaps were placed in separate dissolution vessels, and samples of the buffer in each vessel were obtained at 0.25, 0.5, 1, 2, 3, 6, and 24 hours. The samples were analyzed at 266 and 272 nm on a Perkin Elmer Lambda 20 UV-vis spectrophotometer for AZT and ddC drug content, respectively.

Release of AZT and ddC can be modulated simply by the use of different solvents in the SAIB delivery system. By using a 70:30 SAIB/Migylol® 810 combination, the cumulative percent released at 2 hours for an 11.1 wt % AZT formulation was 104.1% and 74.2% for a 0.225 wt % ddC formulation. Comparatively, when an 85:15 SAIB/EtOH combination was used, 71.2% of the drug in the AZT formulation had been released and 59.5% of the drug in the ddC formulation. Release can also be modified by altering drug loading. When the active loading of an 85:15 SAIB/EtOH formulation was doubled from 11.1 to 22.2 wt %, the cumulative percent released was increased from 71.2% to 93.8%. The use of a polymeric additive, cellulose acetate butyrate (CAB), to modulate release was also evaluated. For an 11.1 wt % AZT in 85:15 SAIB/EtOH formulation, addition of 0.02 and 0.2 wt % CAB decreased the amount released at 2 hours from 71.2% to 25.6% and 7.6%, respectively. For a 0.225 wt % ddC in 85:15 SAIB/EtOH formulation, addition of 0.5 and 1.0 wt % CAB decreased the amount released at 2 hours from 59.5% to 39.4% and 13.5%, respectively.

These data show that formulations of the SAIB delivery system can be modified to provide a range of dissolution profiles for AZT and ddC. By providing controlled release of these actives, this system can reduce the number of pills needed per day, reduce cost of manufacture, and improve patient compliance.

The present invention having been thus described, variations and modifications thereof as would be apparent to those of skill in the art will be understood to be within the scope of the appended claims.

What is claimed is:

1. A liquid composition for the delivery of biologically active substances, comprising:
    a non-water soluble, high viscosity, liquid carrier material comprising a nonpolymeric ester or mixed ester of one or more carboxylc acids, having a viscosity of at least 5,000 cP at 37 C, that does not crystallize neat under ambient or physiological conditions;
    a biological active substance dispersed in the non-water soluble, high viscosity, liquid carrier material;
    wherein when the ester contains an alcohol moiety that is glycerol, the acid moieties do not each consist of a combination of lactic acid moieties and ε-hydroxycaproic acid moieties.

2. The composition of claim 1, wherein at least one of said one or more carboxylic acids is a hydroxy acid.

3. The composition of claim 1, wherein said nonpolymeric ester or mixed ester is obtained by a ring opening reaction of a lactone or a cyclic carbonate.

4. The composition of claim 2, wherein said nonpolymeric ester or mixed ester comprises 2 to about 20 hydroxy acid moieties.

5. The composition of claim 3, wherein said nonpolymeric ester or mixed ester comprises 2 to about 20 hydroxy acid moieties.

6. The composition of claim 1, wherein said nonpolymeric ester or mixed ester of one or more carboxylic acids comprises a polyoxy alcohol moiety having from 2 to about 20 hydroxy moieties.

7. The composition of claim 1, wherein said nonpolymeric ester or mixed ester comprises an alcohol moiety having one or more terminal hydroxy moieties esterified with a carboxylic acid obtained by alcoholysis of a carboxylic acid anhydride.

8. The composition of claim 7, wherein said carboxylic acid anhydride is a cyclic anhydride.

9. The composition of claim 1, wherein said nonpolymeric ester or mixed ester comprises an alcohol moiety having one or more terminal hydroxy moieties esterified with an amino acid.

10. The composition of claim 6, wherein the nonpolymeric ester or mixed ester comprises an alcohol moiety obtained by removing one or more hydrogen atoms from a alcohol selected from the group consisting of: monofunctional $C_1$–$C_{20}$ alcohols, difunctional $C_1$–$C_{20}$ alcohols, trifunctional alcohols, hydroxy-containing carboxylic acids, hydroxy-containing amino acids, phosphate-containing alcohols, tetrafinctional alcohols, sugar alcohols, monosaccharides, and disaccharides, sugar acids, and polyether polyols.

11. The composition of claim 10, wherein the monofunctional $C_1$–$C_{20}$ alcohol is dodecanol.

12. The composition of claim 10, wherein the difunctional $C_1$–$C_{20}$ alcohol is a hexanediol.

13. The composition of claim 10, wherein the trifunctional alcohol is glycerol.

14. The composition of claim 10, wherein the hydroxy-containing carboxylic acid is glycolic acid of latctic acid or a combination thereof.

15. The composition of claim 10, wherein the hydroxy-containing amino acid is serine.

16. The composition of claim 10, wherein the hydroxy-containing acid is hydroxybutyric acid, hydroxyvaleric acid, hydroxycaproic acid, or a mixture of one or more of these.

17. The composition of claim 10, wherein the phosphate containing alcohol is ATP.

18. The composition of claim 10, wherein the terafunctional alcohol is pentaerythritol.

19. The composition of claim 10, wherein the sugar alcohol is mannitol or sorbitol.

20. The composition of claim 10, wherein the monosaccharide is glucose or fructose.

21. The composition of claim 10, wherein the disaccharide is sucrose.

22. The composition of claim 10, wherein the sugar acid is glucuronic acid.

23. The composition of claim 10, wherein the polyether polyol is a polyglycerol ether containing form 1 to about 10 glycerol units or a plyethyleneglycol containing 1 to about 20 ethylene plycol units.

24. The composition of claim 3, wherein the lactone is selected from the group consisting of glycolide, lactide, ε-caprolactone, butyrolactone, valerolactone, and wherein the cyclic carbonate is selected from the group consisting of trimethylene carbonate, propylene carbonate.

25. The composition of claim 1, wherein said biologically active substance is encapsulated within a microsphere.

26. The composition of claim 1, wherein the biologically active substance is selected from the group consisting of a protein, a peptide, a nucleoprotein, a mucoprotein, a lipoprotein, and a synthetic polypeptide.

27. The composition of claim 26, wherein the protein is selected from group consisting of human growth hormone, fibroblast growth factor (FGF), erythropoietin (EPO), platelet derived growth factor (PDGF), granulocyte colony stimulating factor (g-CSF), bovine somatotropin (BST), tumor necrosis factor (TNF), transforming growth factor-beta (TGF-Beta), interleukins, insulin, and interferon.

28. The composition of claim 1, wherein the biologically active substance is selected from the group consisting of nucleic acid, nucleotides, nucleosides, oligonucleotides, and genes.

29. The composition of claim 28, wherein the nucleic acid comprises DNA, RNA, or a fragment thereof.

30. The liquid composition according to claim 1, wherein the high viscosity liquid carrier material has a structure selected from the group consisting of:

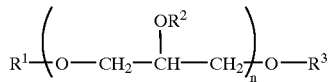

wherein $R^1$, $R^2$, and $R^3$ are independently selected from the group of hydrogen, alkanoyl hydroxy-substituted alkanoyl, and acyloxy-substituted alkanoyl and wherein is between 1 and 20, wherein $R^1$, $R^2$, and $R^3$ do not each consist of a combination of lactic acid moieties and ε-hydroxycaproyl moieties.

31. The composition of claim 30, wherein the high viscosity liquid carrier comprises a structure selected from the group consisting of:

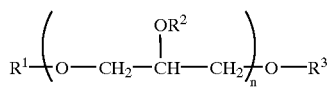

wherein n is 1 and $R^1$, $R^2$, and $R^3$ are independently selected from the group consisting of hydrogen, alkanoyl, hydroxy-substituted alkanoyl, and acyloxy-substituted alkanoyl; and

wherein n is 6, and $R^1$ and $R^2$ are independently selected from the group consisting of hydrogen, alkanoyl, hydroxy-substituted alkanoyl, and acyloxy-substituted alkanoyl.

32. The composition according to claim 31, wherein the high viscosity liquid carrier comprises the structure:

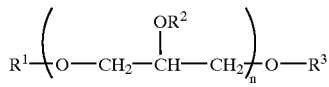

wherein n is 1 and at least one of $R^1$, $R^2$, and $R^3$ are independently selected from the group consisting of hydroxy-substituted alkanoyl, and acyloxy-substituted alkanoyl.

33. The composition according to claim 32, wherein $R^1$, $R^2$, and $R^3$ are independently selected from the group consisting of lactoyl, polylactoyl, ε-caproyl, hydroxyacetyl, and polyhydroxyacetyl.

34. The composition of claim 32, wherein $R^1$, $R^2$, and $R^3$ are independently selected from the group consisting of polylactoyl and ε-caproyl.

35. The composition of claim 33, wherein $R^1$, $R^2$, and $R^3$ are independently selected from the group consisting of polylactoyl and polyhydroxyacetyl.

36. The composition of claim 32, wherein the high viscosity liquid carrier comprises the structure:

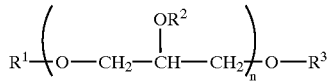

wherein n is 1 and at least one of $R^1$, $R^2$, and $R^3$ are independently selected from the group consisting of alkanoyl, hydroxy-substituted alkanoyl, and acyloxy-substituted alkanoyl, each having from 2 to 4 carbon atoms.

37. The composition of claim 31, wherein the high viscosity liquid carrier comprises the structure:

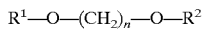

wherein n is 6, and $R^1$ and $R^2$ are independently selected from the group consisting of lactoyl, polylactoyl, ε-caproyl, hydroxyacetyl, and polyhydroxyacetyl.

38. The composition of claim 37, wherein $R^1$ and $R^2$ are independently selected from the group consisting of polylactoyl and ε-caproyl.

39. The composition of claim 37, wherein $R^1$ and $R^2$ are independently selected from the group consisting of polylactoyl and polyhydroxyacetyl.

40. The composition of claim 1, further comprising a solvent for the high viscosity liquid carrier material.

41. The composition of claim 40, wherein the solvent is selected from the group consisting of acetone, benzyl alcohol, benzyl benzoate, N-(betahydromethyl) lactamide, butylene glycol, caprolactam, caprolactone, corn oil, decylmethylsulfoxide, dimethyl ether, dimethyl sulfoxide, 1-dodecylazacycloheptan-2-one, ethanol, ethyl acetate, ethyl lactate, ethyl oleate, glycerol, glycofurol (tetraglycol), isopropyl myristate, methyl acetate, methyl ethyl ketone, N-methyl-2-pyrrolidone, esters of caprylic and/or capric acids with glycerol or alkylene glycols, oleic acid, peanut oil, polyethylene glycol, propylene carbonate, 2-pyrrolidone, sesame oil, [±]-2,2-dimethyl-1,3-dioxolane-4-methanol, tetrahydrofuran, diethylene glycol monoethyl ether, carbitol, triacetin, triethyl citrate, and combinations thereof.

42. The composition of claim 40, wherein the solvent is selected from the group consisting of trichlorofluoromethane, dichlorofluoromethane, tetrafluoroethane (R-134a), dimethyl ether, propane, butane, and combinations thereof.

43. The composition of claim 40, wherein the solvent is selected from the group consisting of benzyl benzoate, dimethyl sulfoxide, ethanol, ethyl lactate, glycerol, glycofurol (tetraglycol), N-methyl-2-pyrrolidone, caprylic/capric triglyceride, polyethylene glycol, propylene carbonate, 2-pyrrolidone, and combinations thereof.

44. The composition of claim 1, wherein the composition is encapsulated within a microsphere.

45. The composition of claim 1, wherein the composition further comprises a biologically active substance encapsulated within a microsphere.

46. The composition of claim 1, wherein the composition is in the form of an emulsion.

47. The composition of claim 1, further comprising an additive.

48. The composition of claim 47, wherein the additive is selected from the group consisting of biodegradable polymers, non-biodegradable polymers, natural oils, synthetic oils, carbohydrates, carbohydrate derivatives, inorganic salts, inert organic compounds, and water.

49. A method of administering a biologically active substance to a plant or animal in need thereof, comprising:

admistering to the plant or animal a composition comprising:

a non-water soluble, high viscosity, liquid carrier material comprising a nonpolymeric ester or mixed ester of one or more carboxylic acids, having a viscosity of at least 5,000 cP at 37° C., that does not crystalize neat under ambient or physiological conditions; and a biologically active substance wherein when the ester contains an alcohol moiety that is glycerol, the acid moieties do not each consist of a combination of lactic acid moieties and $\epsilon$-hydroxycaproic acid moieties.

50. The method of claim 49, wherein the composition further comprises a solvent in which the non-water soluble, high viscosity, liquid carrier material is soluble.

51. The method of claim 50, further comprising allowing said solvent to diffuse or migrate away from said non-water soluble, high viscosity, liquid carrier material, thereby increasing the viscosity of the composition.

52. The method of claim 49, wherein said composition releases said biologically active material from the composition into the tissue of the plant or animal over time.

53. The method of claim 49, wherein said administering comprises administering by injection.

54. The method of claim 49, wherein said administering comprises administering rectally.

55. The method of claim 49, wherein said administering comprises administering intravaginally.

56. The method of claim 49, wherein said administering comprises administering intranasally.

57. The method of claim 49, wherein said administering comprises administering topically.

58. The method of claim 49, wherein said administering comprises pulmonary administration.

* * * * *